United States Patent [19]
Ohtani et al.

[11] Patent Number: 5,817,826
[45] Date of Patent: Oct. 6, 1998

[54] OXAZOLINONE DERIVATIVES HAVING CYTOSOLIC PHOSPHOLIPASE A$_2$ INHIBITORY ACTIVITY

[75] Inventors: Mitsuaki Ohtani, Nara; Toshiyuki Kato, Suita, both of Japan

[73] Assignee: Shionogi & Co., Ltd., Japan

[21] Appl. No.: 905,943

[22] Filed: Aug. 5, 1997

Related U.S. Application Data

[63] Continuation of Ser. No. 454,382, Jun. 15, 1995, abandoned.

[30] Foreign Application Priority Data

Oct. 15, 1993 [JP] Japan .................................. 5-258309

[51] Int. Cl.$^6$ .............................................. C07D 263/38
[52] U.S. Cl. ......................................... 548/229; 548/231
[58] Field of Search ..................................... 548/229, 231

[56] References Cited

U.S. PATENT DOCUMENTS

| | | |
|---|---|---|
| 2,975,187 | 3/1961 | Lynn . |
| 3,033,829 | 5/1962 | Bakke . |
| 3,152,141 | 10/1964 | Tousignant . |

FOREIGN PATENT DOCUMENTS

| | | |
|---|---|---|
| 51-75521 | 6/1976 | Japan . |
| 52-010874 | 3/1977 | Japan . |
| 52-97966 | 8/1977 | Japan . |
| 53-146635 | 12/1978 | Japan . |
| 61-286375 | 12/1986 | Japan . |
| 3-500298 | 1/1991 | Japan . |
| 5-239078 | 9/1993 | Japan . |
| WO91/06538 | 5/1991 | WIPO . |

OTHER PUBLICATIONS

R. Gomper et al., *Berichte der Deutschen Chemischen Gesellschaft*, 89(7), 1749–1762(1956).
H. Zimmerman et al., *Journal of the American Chemical Society*, 79(8), 1920–1923(1957).
H. Greenberg et al., *Journal of Organic Chemistry*, 32(10), 2964–2966(1967).
J. Lemmens et al., *Journal of Organic Chemistry*, 49(12), 2231–2235(1984).
H. Lautenschläger, *Justus Liebigs Annalen der Chemie*, 4, 566–572(1978).
G. Hakimelahi et al., *Helvetica Chimica Acta*, 60(2), 342–347(1977).
T. van Es et al., *Journal of the Chemical Society*, 1963 Letchworth GB, 1363–1370(1963).
K. Mehrotra et al., *Bulletin of the Chemical Society of Japan*, 58(8), 2399–2402(1985).
M. Pinchas et al., *Chemical Abstracts*, 90(13), Abstract No. 97468c(1979).
S. Shibuya, *Heterocycles*, 23(2), 395–398(1985).
C. Busacca et al., *J. Org. Chem.*, 58(12), 3299–3303(1993).
A. Padwa et al., *J. Org. Chem.*, 49(3), 399–406 (1984).
F. Guziec et al., *J. Heterocycl. Chem.*, 17(8), 1807–1808(1980).
*Chemical Abstracts*, 86, Abstract No. 189783(1977).
*Chemical Abstracts*, 103, Abstract No. 22883(1985).
*Chemical Abstracts*, 91, Abstract No. 176651(1979).
*Chemical Abstracts*, 86, Abstract No. 29695(1977).
*Chemical Abstracts*, 63, Abstract No. 11542h(1965).

*Primary Examiner*—Robert Gerstl
*Attorney, Agent, or Firm*—Wenderoth, Lind & Ponack

[57] ABSTRACT

The present invention relates to a compound represented by the formula:

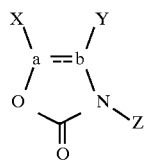

wherein a and b are each a carbon atom;
a bond:
- - - - -
between a and b indicates that it is a single bond or a double bond;

X is a hydrogen atom, an optionally substituted aryl group, an optionally substitued heteroaryl group, or an optionally substituted aralkyl group;

Y is a hydrogen atom, an optionally substituted aryl group, an optionally substituted aralkyl group, or a carboxyl group or related functional groups thereof; and Z is a hydrogen atom, an optionally substituted alkyl group, an optionally substituted alkenyl group, an optionally substituted alkynyl group, an optionally substituted aralkyl, an optionally substituted arylalkenyl group, an optionally substituted heteroarylalkyl group, an optionally substituted heteroarylalkenyl group, an optionally substituted aryloxyalkyl group, an optionally substituted aralkyloxyalkyl group, an optionally substituted arylcarbonylalkyl group, an optionally substituted arylsulfonylalkyl group, an optionally substituted heteroarylsulfonylalkyl group, an optionally substituted aminoalkyl group, an optionally substituted carboxyalkyl group or related functional groups thereof, an optionally substituted alkyloxycarbonyl group, an optionally substituted aralkyloxycarbonyl group, an optionally substituted arylcarbonyl group, an optionally substituted alkylsulfonyl group, an optionally substituted arylsulfonyl group, or an optionally substituted heteroarylsulfonyl group; provided that X, Y and Z are not a hydrogen atom at the same time, and a pharmaceutical composition containing the same. The compounds of the present invention have a cytosolic phospholipase A$_2$ inhibitiory activity.

1 Claim, No Drawings

OXAZOLINONE DERIVATIVES HAVING CYTOSOLIC PHOSPHOLIPASE A₂ INHIBITORY ACTIVITY

This application is a continuation of now abandoned application Ser. No. 08/454,382, filed Jun. 15, 1995, which is a 371 of PCT/JP94/01716, filed Oct. 13, 1994.

INDUSTRIAL UTILIZATION FIELD

The present invention relates to oxazolinone derivatives having a cytosolic phospholipase A₂ inhibitory activity, and cytosolic phospholipase A₂ inhibitors containing the oxazolinone derivatives. More particularly, it relates to oxazolin-2-one and oxazolidin-2-one derivatives having the activity, and cytosolic phospholipase A₂ inhibitors containing the derivatives.

BACKGROUND OF THE INVENTION

Phospholipase A₂ (PLA₂) is a protein which hydrolyzes a 2-acyl ester bond of phospholipids, and examples thereof include cytosolic PLA₂ and secretory PLA₂ which can be clearly distinguished from each other. It has been known that the cytosolic PLA₂ (cPLA₂) selectively hydrolyzes phospholipids containing arachidonic acid of which 2-position is esterified.

PRIOR ART AND PROBLEMS TO BE SOLVED BY THE INVENTION

Various oxazolinone derivatives have already been disclosed, and they are described as having a central muscular relaxant action or a phospholipase A₂ inhibitory action [Japanese Patent Publication (kokai) No. 61-286375, U.S. Pat. No. 5,071,988 and Japanese Patent Publication (koukoku) No. 52-10874].

However, any of the publications mentioned above does not decribe about the cytosolic PLA₂ and they don't even suggest oxazolinone derivatives having cytosolic PLA₂ inhibitory action.

Heretofore, the cytosolic PLA₂ has never been purified in high purity, and therefore, the PLA₂ inhibitiory action of the oxazolione derivatives has never been reported.

The present inventors have paid attention to an interesting activity of cPLA₂, and have developed a substance useful for treating inflammatory diseases by inhibiting the activity. Since the compounds of the present invention inhibit the action of cPLA₂, the liberation of arachidonic acid from the phospholipid is prevented, thereby inhibiting the formation of various prostaglandins, leukotrienes, etc., which are referred to as "arachidonic acid cascade". Accordingly, it is expected that the compounds of the present invention decrease the action of transmitter substances of inflammation.

MEANS OF SOLVING THE PROBLEMS

The present invention relates to a compound represented by the formula:

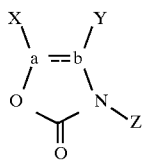

wherein a and b are each indicate a carbon atom;

a bond: 

between a and b indicates that it is a single bond or a double bond;

X is a hydrogen atom, an optionally substituted aryl group, an optionally substitued heteroaryl group, or an optionally substituted aralkyl group;

Y is a hydrogen atom, an optionally substituted aryl group, an optionally substituted aralkyl group, or a carboxyl group or related functional groups thereof; and Z is a hydrogen atom, an optionally substituted alkyl group, an optionally substituted alkenyl group, an optionally substituted alkynyl group, an optionally substituted aralkyl, an optionally substituted arylalkenyl group, an optionally substituted heteroarylalkyl group, an optionally substituted heteroarylalkenyl group, an optionally substituted aryloxyalkyl group, an optionally substituted aralkyloxyalkyl group, an optionally substituted arylcarbonylalkyl group, an optionally substituted arylsulfonylalkyl group, an optionally substituted heteroarylsulfonylalkyl group, an optionally substituted aminoalkyl group, an optionally substituted carboxyalkyl group or related functional groups thereof, an optionally substituted alkyloxycarbonyl group, an optionally substituted aralkyloxycarbonyl group, an optionally substituted arylcarbonyl group, an optionally substituted alkylsulfonyl group, an optionally substituted arylsulfonyl group, or an optionally substituted heteroarylsulfonyl group; provided that X, Y and Z are not a hydrogen atom at the same time.

However, the compounds represented by the following formulas are excluded from the present invention.

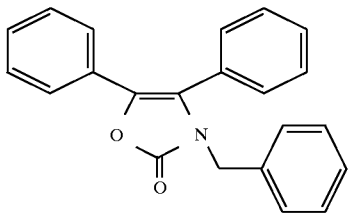

0001

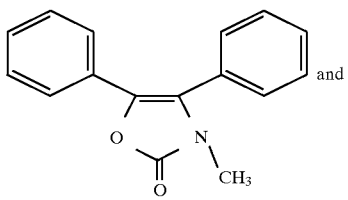

and

0002

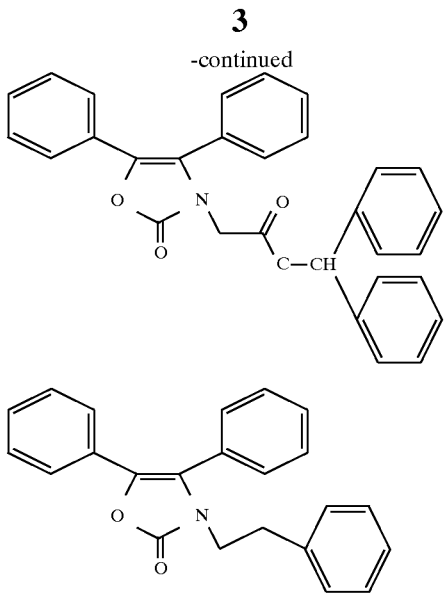

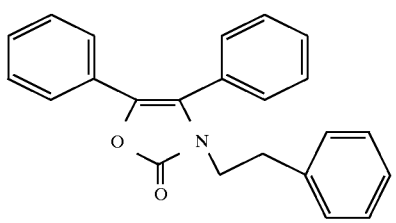

In the compounds represented by the above formulas wherein the bond between a and b is a single bond, stereoisomers may exist, and all optically active substances and a mixture thereof are included in the compounds of the present invention.

The compounds of the present invention can be classified into the following categories:

1) compounds wherein X and Y independently are an optionally substituted phenyl or thienyl group, and
    Z is an optionally substituted aralkyl group, an optionally substituted heteroarylakyl group, an optionally substituted aryloxyalkyl group, an optionally substituted aralkyloxyalkyl group, an optionally substituted arylcarbonylalkyl group, or an optionally substituted arylsulfonyl group provided that Z is not benzyl or phenethyl;

2) compounds wherein X and Y independently are an optionally substiuented phenyl group, and
    Z is an optionally substituted alkyl group, an optionally substituted alkenyl group or an optionally substituted alkynyl group provided that Z is not methyl;

3) compounds wherein the bond between a and b is a double bond, and
    X and Y independently are an optionally substituted phenyl group; Z is a group represented by the formula:

—(CH$_2$)$_n$NR$^1$R$^2$ wherein n is 1, 2, or 3; and R$^1$ and R$^2$ are the same or different and are a C$_1$–C$_4$ alkyl group, or a group of the formula:

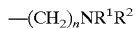

wherein R$^4$ is a C$_1$–C$_4$ alkyl group or an optionally substituted phenyl group, or a group of the formula:

—(CH$_2$)$_n$N$^+$R$^1$R$^2$R$^3$X$^-$ wherein n is 1 or 2; R$^1$ and R$^2$ are as defined above; R$^3$ is a C$_1$–C$_4$ alkyl; and X is a halogen atom;

4) compounds wherein the bond between a and b is a double bond,
    X is a phenyl group optionally substituted with a sulfonylhydrazide group, a sulfonamide group, a phenyl group or —SO$_3$H,
    Y is a phenyl group, and
    Z is a hydrogen atom; provided that X is not a phenyl group substituted with —SO$_2$NH$_2$;

5) compounds wherein the bond between a and b is a double bond,
    X and Y are the same and are a phenyl group substituted with a carboxyl group or related functional group or groups, and
    Z is a hydrogen atom provided that X and Y are not a phenyl group substituted with —COCl;

6) compounds wherein the bond between a and b is a double bond,
    X is a phenyl group;
    Y is a phenyl group substituted with a phenyl group, and
    Z is a hydrogen atom;

7) compounds wherein the bond between a and b is a double bond,
    X is an optionally substituted phenyl group or an optionally substituted aralkyl group,
    Y is a hydrogen atom, and
    Z is a hydrogen atom, an optionally substituted alkyl group, an optionally substituted alkenyl group or an optionally substituted alkynyl group, provided that when X is phenyl, Z is not a hydrogen atom;

8) compounds wherein the bond between a and b is a double bond,
    X is an optionally substituted phenyl group or an aralkyl group,
    Y is a hydrogen atom, and
    Z is an optionally substituted aralkyl group, an optionally substituted heteroarylalkyl group, an optionally substituted aryloxyalkyl group or an optionally substituted aralkyloxycarbonyl group;

9) compounds wherein the bond between a and b is a double bond,
    X is a phenyl group,
    Y is a carboxyl group or related functional groups thereof, and
    Z is a hydrogen atom or an optionally substituted aralkyl group, provided that when Y is —COOCH$_3$, Z is a not hydrogen atom;

10) compounds wherein the bond between a and b is a single bond, and
    X is a hydrogen atom; especially, compounds wherein the bond between a and b is a single bond, and X is a hydrogen atom, and Y is an optionally substituted aralkyl group, and Z is an optionally substituted alkenyl group.

In the above formulas, examples of the "aryl group" in the "optionally substituted aryl group" include phenyl, naphthyl and the like. Among them, phenyl is preferred. The term "aralkyl group" in the "optionally substituted aralkyl group" means that optionally branched C$_1$–C$_6$ alkyl groups which are substituted with aryl group(s), and examples thereof include benzyl, phenethyl, phenylpropylphenylbutyl, (α- or β-) naphthylmethyl and the like. Among them, benzyl is preferred. The term "heteroaryl group" in the "optionally substituted heteroaryl group" means 5- or 6-membered heterocycles having aromaticity, which contains at least one nitrogen, oxygen and/or sulfur in the ring. These may be condensed with a benzene ring. Examples thereof include thienyl, furyl, pyrrolyl, imidazolyl, pyrazolyl, pyridyl, pyrimidinyl, quinolyl, isoxazolyl and the like. Among them, thienyl is preferred. Examples of the "substituent" in the "optionally substituted aralkyl group" or "optionally substituted heteroaryl group" include alkyl, alkoxy, halogen, phenyl and the like, and one or more substituents as mentioned above can be substituted on the groups.

Examples of the "carboxyl group or related functional groups thereof" in Y include groups represented by the formulas:

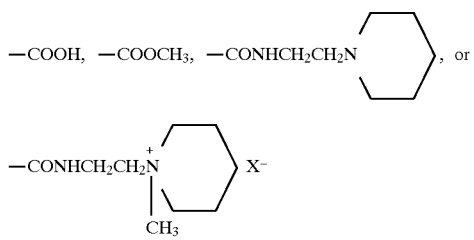

Among them, preferred groups are those represented by the formulas:
—COOH, —COOCH₃, and

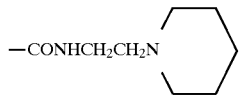

The "optionally substituted aryl group" and "aralkyl group" in Y are as defined in X, and preferred examples of Y include a hydrogen atom or a phenyl group.

Examples of the "substituent" in the "optionally substituted aryl group" include a sulfonylhydrazide group, sulfonamide group, carboxyl group or related functional groups thereof, halogen, alkyl, alkoxy, aryl, SO₃H, SO₂Cl, SO₂O(CH₂)₃Br and the like.

Examples of the "sulfonylhydrazide group" include the groups represented by the formulas:

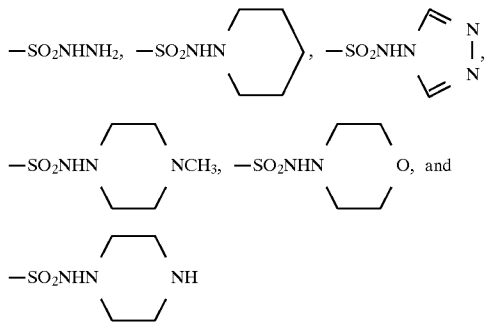

Among them, preferred group is that represented by the formula:

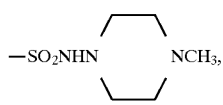

Examples of the "sulfonamide group" include sulfonamides containing amino derivatives such as ammonia, pyrrolidine, piperidine, piperazine, morpholine, N-methylpiperazine, N-aralkylpiperazine, N-alkylsulfonylpiperazine, N-arylsulfonylpiperazine, piperidylalkylamine, piperazylalkylamine, morpholylalkylamine, N-alkylpiperidylamine, N-aralkylpiperidylamine, pyridiniumalkylamine, carboxyphenylamine, carbamoylphenylamine, bromoalkylamine and the like. Preferred "sulfonamide groups" are groups represented by the formulas:

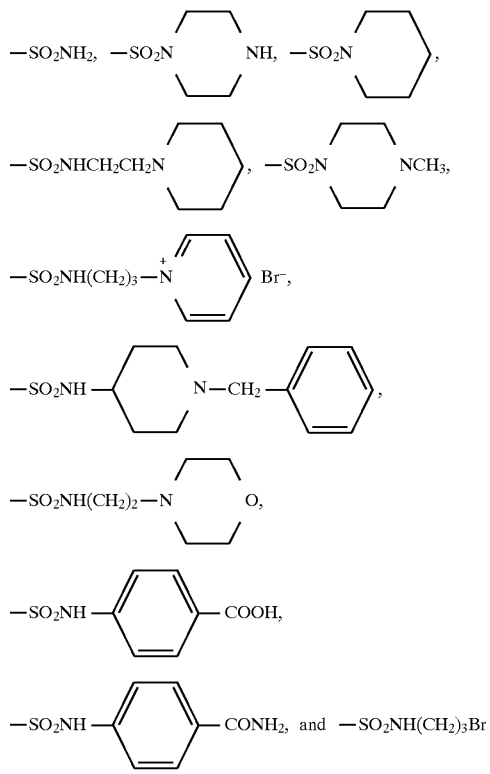

More preferred group is a group represented by the formula:

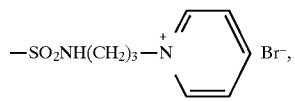

Examples of the carboxyl group or a related functional group thereof include groups represented by the formulas:

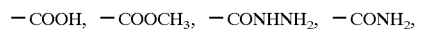
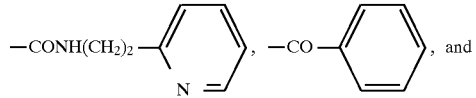

Among them, preferred group is a carboxyl group.

"Halogen" means a group such as fluorine, chlorine, bromine and the like.

"Alkyl" means a straight-chain or branched $C_1$–$C_6$ alkyl, and examples thereof include methyl, ethyl, propyl and the like.

"Alkoxy" means a straight-chain or branched $C_1$–$C_6$ alkoxy, and examples thereof include methoxy, ethoxy, propoxy, butoxy, bromobutoxy and the like.

Examples of the "aryl group" include phenyl, naphthyl and the like,

In the definition of Z, the "alkyl group" in the "optionally substituted alkyl group" means a straight-chain or branched $C_1$–$C_6$ alkyl, and examples thereof include methyl, ethyl, n-propyl, i-propyl, n-butyl, i-butyl, n-pentyl, i-pentyl, n-hexyl, neohexyl and the like.

The "alkenyl group" in the "optionally substituted alkenyl group" means a straight-chain or branched $C_2$–$C_{15}$ alkenyl, and examples thereof include vinyl, allyl, propenyl, butenyl, pentenyl, prenyl, geranyl, flunesyl, neryl, 3,7-dimethylocten-6-yl and the like. The "alkynyl group" means a straight-chain or branched $C_2$–$C_7$ alkynyl, and examples thereof include ethynyl, 1- and 2-propynyl, 1-, 2- and 3-butynyl and the like. The "aralkyl group" in the "optionally substituted aralkyl group" is as defined in the X, and preferred aralkyl group is a benzyl.

Examples of the "optionally substituted aminoalkyl group" include groups represented by the formulas:

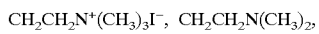

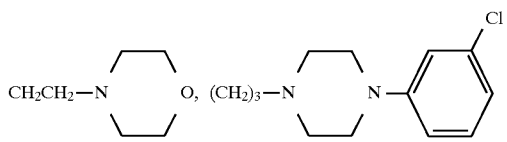

Examples of the "optionally substituted carboxyalkyl group or related functional groups thereof" include —$CH_2COOH$, —$CH_2COOCH(C_6H_5)_2$, —$(CH_2)_2COOCH(C_6H_5)_2$ and the like. Examples of the "optionally substituted alkyloxycarbonyl group" include —$COOtBu$ and the like. Examples of the "optionally substituted aralkyloxycarbonyl group" include groups represented by the formulas:

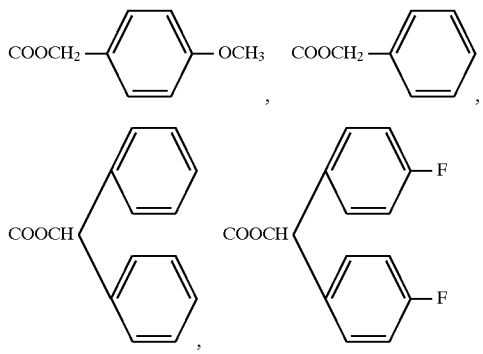

Examples of the "optionally substituted arylcarbonyl group" include groups represented by the formulas:

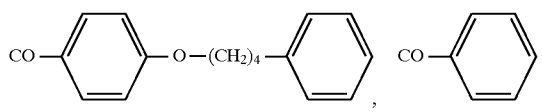

and the like.

The "alkylsulfonyl group" in the "optionally substituted alkylsulfonyl group" means a $C_1$–$C_6$ alkylsulfonyl group, and examples thereof include methylsulfonyl, ethylsulfonyl, propylsulfonyl, butylsulfonyl, pentylsulfonyl, hexylsulfonyl and the like. Examples of the "arylsulfonyl group" in the "optionally substituted arylsulfonyl group" include phenylsulfonyl, α- and β-naphthylsulfonyl and the like. Examples of the "heteroarylsulfonyl group" in the "optionally substituted heteroarylsulfonyl group" include thienylsulfonyl, furylsulfonyl, pyrrolylsulfonyl, imidazolylsulfonyl, pyrazolylsulfonyl, pyridylsulfonyl, pyrimidinylsulfonyl, quinolylsulfonyl, isoxazolylsulfonyl and the like.

Examples of the "substituent" in the "optionally substituted alkyl group", "optionally substituted alkenyl group", "optionally substituted alkynyl group" and "optionally substituted aralkyl group" include $C_1$–$C_4$ alkyl group, $C_3$–$C_6$ cycloalkyl group, $C_1$–$C_3$ alkoxy group, methoxycarbonyl group, phenyl group, halogen atom, carboxyl group, nitro group and the like, and one or more substituents can be substituted thereon.

The heteroaryl moiety, aryl moiety and aralkyl moiety in the "optionally substituted arylalkenyl group", "optionally substituted heteroarylalkyl group", "optionally substituted heteroarylalkenyl group", "optionally substituted aryloxyalkyl group", "optionally substituted aralkyloxyalkyl group", "optionally substituted arylcarbonylalkyl group", "optionally substituted arylsulfonylalkyl group", and "optionally substituted heteroarylsulfonylalkyl group" are as defined in X. The alkenyl moiety and alkyl moiety thereof are as defined in Z. Examples of the "substituent" as mentioned above include one or more substituents selected from alkyl, alkoxy, halogen, phenyl, trifluoromethyl and the like.

The compounds of the present invention can be synthesized according to a conventional method. Hereinafter, a general synthetic method of the compounds of the invention will be explained.

I. Oxazolinone derivatives

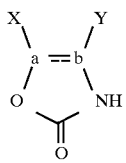

A

1) Bond between a and b: double bond (oxazolin-2-one derivatives) 1)-i X═Y=aryl group or aralkyl group The compounds of the present invention can be mainly synthesized according to any one of the methods described in the published literatures [G. H. Hakimelahi, C. B. Boyce and H. S. Kasmai, Helvetica Chim. Acta 60, 342 (1977)].

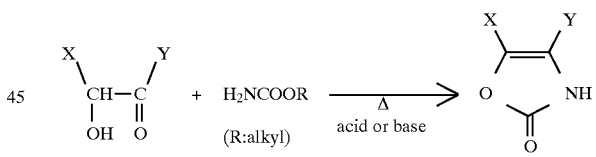

B                                                      C

That is, a bezoin compound B and a carbamate ester are heated in the presence of a base or an acid to give the objective product C. X and Y may be an aryl group or an aralkyl group other than a benzene ring, and the ester residue of carbamic acid may be an alkyl, aryl and aralkyl group, such as methyl, ethyl, propyl, phenyl, benzyl and the like. The acid to be used as a catalyst may be an acid such as hydrochloric acid, sulfuric acid, polyphosphoric acid, toluenesulfonic acid, phosphoric acid and the like. As the basic catalyst, there can be used pyridine, triethylamine, 4,4-dimethylaminopyridine, N,N-diisopropylethylamine, 1,5-diazabicyclo[4.3.0]non-5-ene (DBN), 1,4-diazabicyclo[2.2.2]octane (DABCO), 1,8-diazabicyclo[5.4.0]undece-7-ene (DBU), potassium carbonate, sodium carbonate, potassium hydroxide, sodium hydroxide and the like.

This reaction can be normally completed by heating the reaction mixture at 60° C.~200° C., preferably at 100°

C.~180° C., for 1 hour~48 hours, preferably for 8 hours~30 hours. As the solvent, there can be used N,N-dimethylformamide (DMF), dimethyl sulfoxide (DMSO) and the like, but the objective product can be obtained in good yield in the absence of the solvent.

1)-ii X≠Y: X, Y=aryl group or aralkyl group

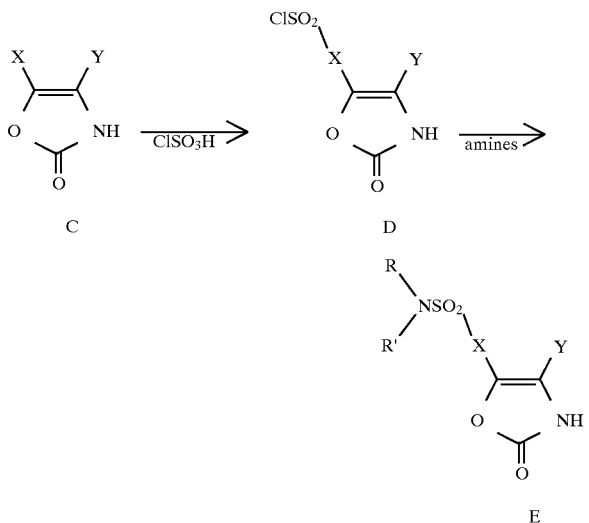

In the reaction scheme, only chlorosulfonylation is shown, but acylation, alkylation, chlorocarbonylation, halogenation, nitration, etc. can occur, similarly.

Regarding 5-(4'-sulfonylphenyl) derivative, 4,5-diaryloxazolin-2-one C obtained in the above method 1)-i) is reacted with chlorosulfonic acid to form a 5-chlorosulfonylaryl derivative D which is then reacted with various amines to give a sulfonamide derivative E. NOE determination on $^1$H NMR using a chlorosulfonyl derivative D has revealed that the chlorosulfonation occurs on the aromatic ring X but does not occure on Y in this reaction.

The chlorosulfonation can be accomplished by reacting at 0° C.~100° C., preferably at 20° C.~60° C., for 1 hour~6 hours in the presence of a solvent such as $CHCl_3$, $CH_2Cl_2$ and the like. Examples of amines which lead to the sulfonamide derivatives include ammonia, pyrrolidine, piperidine, piperazine, morpholine, N-methylpiperazine, piperidylalkylamine, morpholylalkylamine, N-alkylpiperidineamine, N-aralkylpiperidylamine, pyridiniumalkylamine, carboxyphenylamine, carbamoylphenylamine, hydrazine, 1-aminopyrrolidine, 1-aminopiperidine, 4-amino-1,2,4-triazole, 1-amino-4-methylpiperazine, 4-aminomorpholine, 1,4-diaminopiperadine, and amino or hydrazine derivatives which are generally used.

In addition to these sulfonamide compounds, oxazolin-2-one derivatives wherein X≠Y (X and Y respectively indicate an aryl group or aralkyl group) can be obtained by a method described in the published literature [B. Zwanenburg et al., J. Org. Chem., 49, 2231 (1984)].

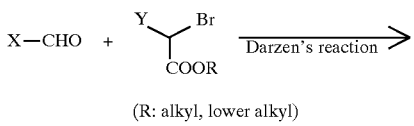

(R: alkyl, lower alkyl)

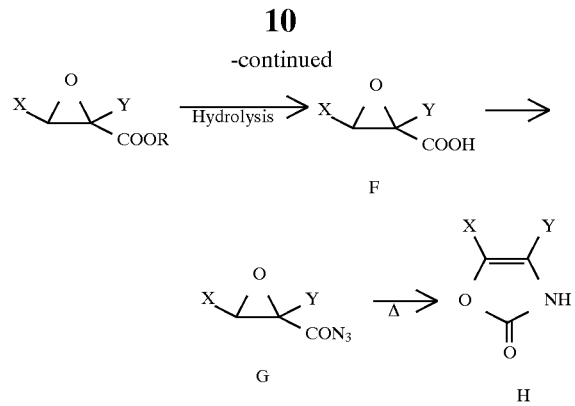

That is, an aldehyde derivative and an α-bromo ester derivative are subjected to the Darzen's reaction in the presence of a base such as sodium alkoxide, lithium diisopropylamide, etc. and the resulting epoxide is hydrolyzed to give carboxylic acid F. This carboxylic acid is activated by leading to acid chloride or active ester, using thienyl chloride, phosphoryl chloride, phosphorous pentachloride, alkylchloroformate, oxalyl chloride, carbodiimide derivative, N-hydroxysuccinimide derivative, N-hydroxybenzotriazole derivative and the like. Then, it was converted into a carbonylazide derivative G with sodium azide or trimethylsilyl azide, and the carbonylazide derivative is subjected to the rearrangement-ring opening reaction with heating to give an oxazolin-2-one derivative H as the objective product. 1)-iii) X≠Y: X=aryl group, Y=carboxylic acid residue Oxazolin-2-ones containing a carboxyl group or related functional groups at the 4-position can be synthesized by a method of C-g. Shin et al. [Chem. Lett, 1171 (1982)].

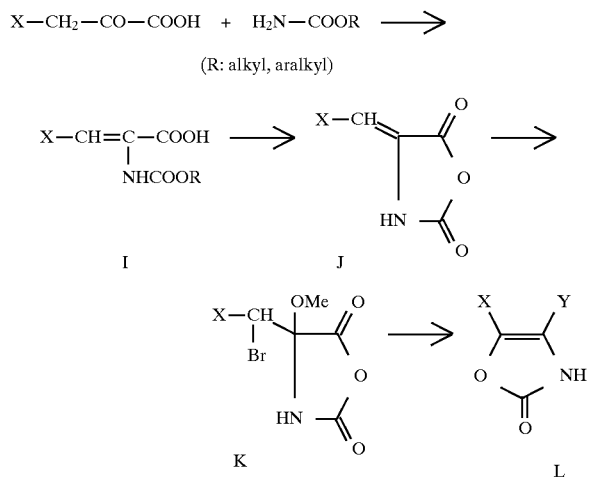

That is, α-dehydroamino acid I obtained from a pyruvic acid derivative and carbamates is reacted with acetyl chloride or thionyl chloride to give a cyclic anhydride J. The resulting cyclic anhydride is reacted with a halogenating agent such as N-bromosuccininide (NBS), N-chlorosuccinimide (NCl), etc. in an alcohol solvent such as methanol etc. to give a product K which is converted, using an organic base (e.g. pyridine, triethylamine, N,N-dimethylaminopyridine (DMAP), DBN, DABCO, DBU, etc.) or an inorganic base (e.g. potassium carbonate, sodium carbonate, potassium hydroxide, sodium hydroxide, etc.), to give the objective compound L. In the above structural formulas, Y is a carboxylate group such as methyl ester, etc.

Another compound of the present invention can be produced by hydrolyzing the resulting compound L to convert into carboxylic acid derivatives such as various amides.

2) Bond between a and b: single bond (oxazolidin-2-one derivative)

The synthesis of the compounds of the present invention can be accomplished by cyclization of various 2-amino alcohol derivatives and converting the same to oxazolidin-2-ones using suitable reagents or reactions. It is apparent that two (when X or Y is a hydrogen atom) or four optically active substances of oxazolidin-2-ones can be synthesized stereoselectively by selecting optically active 2-amino alcohols. These optically active 2-amino alcohols can be synthesized by applying the method of S. D. Burke et al. (Tetr. Lett., 28, No. 34, 3105, 1987), which comprises synthesizing a mono-protected vicinal-glycols from optically active α-alkoxy esters, to the amino acid esters.

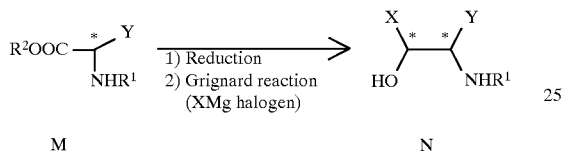

$R^1$: Amino protective group
$R^2$: Alkyl or lower alkyl

In this reaction, an ester is firstly reduced to give an aldehyde intermediate which is then subjected to Grignard reaction in one pot without isolating it. In this case, the aldehyde as the intermediate forms a chelation by a reducing agents-derived metal, and the stereochemistry of the following Grignard reaction is controlled by a structural specificity of this chelation. Accordingly, the stereochemistry of 2-amino ethanols as the product can be controlled by the nature of a metal hydride as the reducing agent. Examples of the reducing agent include lithium borohydride, lithium tri-tert-butoxy aluminum hydride, diisobutyl aluminum hydride, etc., and metal hydrides which are normally used for reducing esters to aldehydes. As the Grignard reagent, there can be used any one which can introduce a substituent X (XM halogen) at the 5-position of oxazolin-2-ones in the following process, and typical examples thereof include phenylmagnesium bromide and the like. As the reaction solvent, there can be used ether solvents such as ether, tetrahydrofuran, dimethoxyethane and the like, and the reaction is normally conducted at −100° C.~−40° C., preferably at −78° C.~0° C.

Some of these 2-amino alcohols are commercially available and can be used as a synthetic starting material for oxazolidin-2-ones of the present invention.

Then, the ring-closure will be conducted to convert 2-amino alcohols into oxazolidin-2-ones. Almost all of cases, they are subjected to the ring-closure in a solvent (e.g. ether, tetrahydrofuran, methylene chloride, benzene, toluene, etc.) at 0° C.~30° C. in the presence of a base which is normally used (e.g. triethylamine, pyridine, etc.), using phosgene or its stable derivative thereof, e.g. triphosgene.

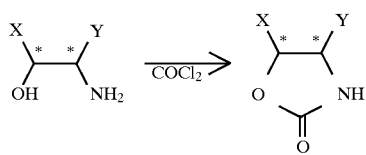

Among 2-amino alcohols, a compound N' which is protected with a carbamate type amino protective group such as a carbobenzoxy group can be converted into oxazolidin-2-ones by subjecting it to the ring-closure under a basic condition according to the method of S. Kano et al. [Tetr. Left., 28, No. 50, 6331 (1987)].

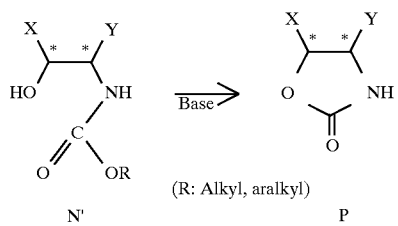

(R: Alkyl, aralkyl)

They are reacted in tetrahydrofuran, water, methanol or a suitable mixed solvent thereof at 0° C.~30° C., using metal hydroxides (e.g. NaOH, KOH, etc.) or organic bases which are normally used (e.g. triethylamine, DBU, etc.) as a base.

II. N-substituted oxazolinone derivative

II-1) The N-substitution reaction is conducted using oxazolin-2-ones thus obtained as described above or oxazolidin-2-ones according to the method described in the published literature [G. H. Hakimelahi et al., Helv. Chim. Acta, 60, 342 (1977)].

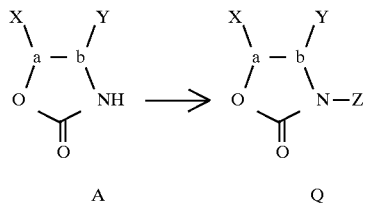

That is, an oxazolin-2-one derivative A is reacted with various halides such as alkyl halide, alkenyl halide, alkynyl halide, aralkyl halide, alkyloxycarbonyl halide, aralkyloxycarbonyl halide, arylcarbonyl halide, alkylsulfony halide, arylsulfonyl halide, etc. in the presence of a strong base such as sodium hydride, n-butyllithium, potassium hydride, potassium t-butoxide, lithium diisopropylamide, sodium amide, etc. to give the objective product Q. Examples of the solvent include tetrahydrofuran, diethyl ether, dioxane, benzene, toluene, dimethylformamide (DMF), dimethylacetamide (DMA), dimethoxyethane, dimethyl sulfoxide (DMSO) and the like. This reaction is conducted at −78° C.~100° C., preferably at −20° C.~60° C.

II-2) N-substituted oxazolin-2-ones can also be synthesized by a method of introducing an amino compound using a cyclic carbonate R as a starting material [J. C. Sheehan et al., J. Org. Chem., 38, No.17, 3034 (1973)], in addition to the N-substitution reaction described in the above item (1).

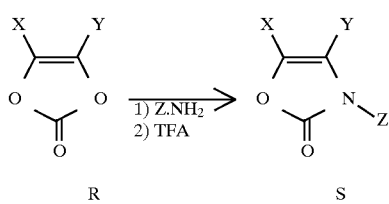

A benzoin derivative and cyclic carbonate R synthesized from phosgene are reacted with various amines, then with trifluoroacetic acid (TFA) to give oxazolin-2-ones S. The reaction between carbonate and amine is generally conducted at about room temperature in DMF. The resulting unstable intermediate is also converted into oxazolin-2-one S at room temperature in TFA. According to this method, a compound, which can not be easily prepared by the reaction between oxazolin-2-ones and halides as described in the item II-1), can be easily synthesized.

III. Ammonium derivatives

Quaternary salts are synthesized by a normal method, for example, by reacting halides as a starting material with amines or reacting amines as a starting material with alkyl halides. As the solvent, there can be used methanol, ethanol, tetrahydrofuran, methylene chloride, diethyl ether, etc., and the reaction is normally conducted within a range from about room temperature to about 100° C.

Further, the present invention relates to a phospholipase $A_2$ inhibitor containing a compound represented by the formula:

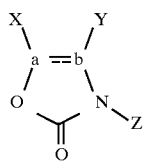

wherein a and b are each a carbon atom;
a bond:
- - - - -
between a and b indicates that it is a single bond or a double bond;

X is a hydrogen atom, an optionally substituted aryl group, an optionally substitued heteroaryl group, or an optionally substituted aralkyl group;

Y is a hydrogen atom, an optionally substituted aryl group, an optionally substituted aralkyl group, or a carboxyl group or related functional groups thereof; and Z is a hydrogen atom, an optionally substituted alkyl group, an optionally substituted alkenyl group, an optionally substituted alkynyl group, an optionally substituted aralkyl, an optionally substituted arylalkenyl group, an optionally substituted heteroarylalkyl group, an optionally substituted heteroarylalkenyl group, an optionally substituted aryloxyalkyl group, an optionally substituted aralkyloxyalkyl group, an optionally substituted arylcarbonylalkyl group, an optionally substituted arysulfonylalkyl group, an optionally substituted heteroarylsulfonylalkyl group, an optionally substituted aminoalkyl group, an optionally substituted carboxyalkyl group or related functional groups thereof, an optionally substituted alkyloxycarbonyl group, an optionally substituted aralkyloxycarbonyl group, an optionally substituted arylcarbonyl group, an optionally substituted alkylsulfonyl group, an optionally substituted arylsulfonyl group, or an optionally substituted heteroarylsulfonyl group; provided that X, Y and Z are not a hydrogen atom at the same time; together with and a pharmaceutically acceptable carrier.

It will be understood that pharmaceutical compositions of the present invention also include pharmaceutical compositions containing known compounds represented by the following formulas:

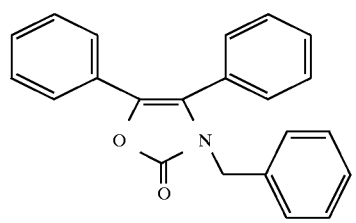

0001

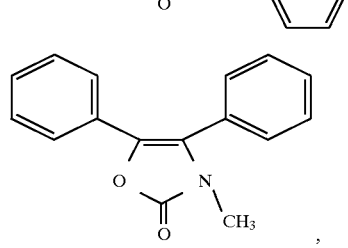

0002

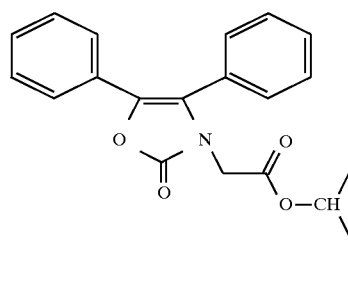

0003 and

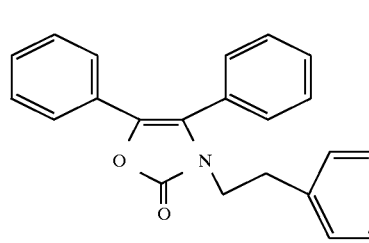

0075

The experiments carried out by the present inventors have revealed, for the first time, that these known compounds also have a cytosolic $PLA_2$ inhibitory activity.

The production process of the known compound 0003 will be explained in Reference Example 1 described hereinafter. Further, the known compounds 0001 and 0002 can be easily produced according to the process of Reference Example 1.

The pharmaceutical compositions of the present invention can be orally or parenterally administered, and therefore, they can be formulated in the form such as oral preparations, injections, ointments and the like.

The dose of the compounds of the present invention varies depending upon the objective therapeutic effect, administration route, patient's age and weight, severity of diseases and the like. The daily dose is generally 50 mg~1000 mg and is generally administered 2 to 5 times per day. Accordingly, the pharmaceutical compositions of the present invention can be formulated in an unit dosage form containing the divided dose.

The following Examples to produce the compounds of the present invention as well as Reference Examples further illustrate the present invention in detail. However, they are not to be construed to limit the scope of the present invention.

The abbreviations used in Examples and Reference Examples have the following meanings. "Nujol" is nujol, "neat" is thin layer, "base peak" is base peak, "MeOH" is methanol, ""EtOH" is ethanol, "EtOAc" or "AcOEt" is ethyl acetate, "DMSO" is dimethyl sulfoxide, "DMF" is N,N'-dimethylformamide, "THF" is tetrahydrofuran, "eq" is equivalent and "Ph" is phenyl group, respectively.

EXAMPLE 1

Synthesis of 5-[4-(4-methyl)piperazinylsulfenyl]phenyl-4-phenyl-2-oxazolone (0037)

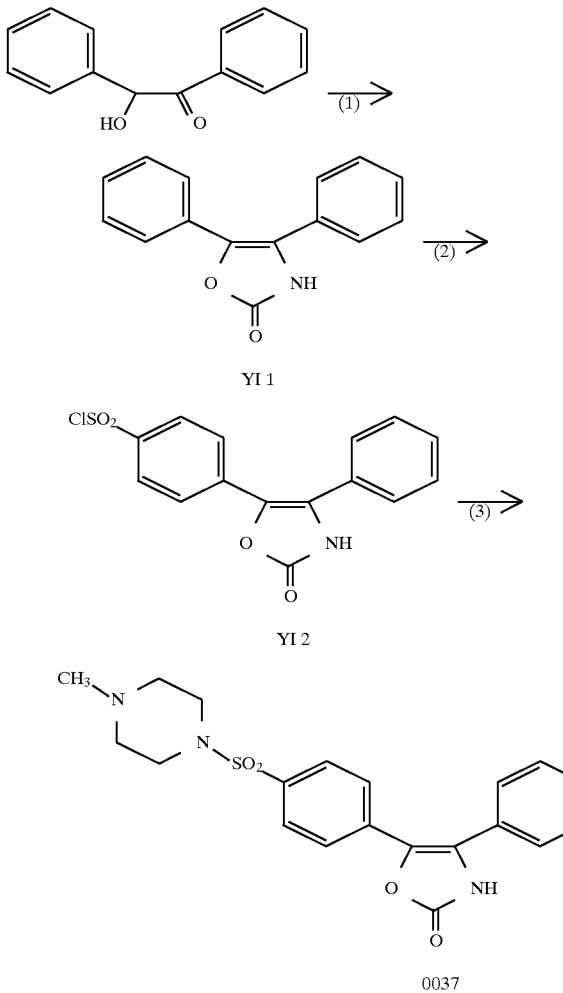

(1) A mixture of benzoin (213 g, 1.0 mol), urethane (445 g, 5.0 mol) and pyridine (80 ml) was heated to 160° C. and dissolved, then stirred at the same temperature for 18 hours. Ethanol produced by the reaction was distilled off under reduced pressure and, after pyridine (80 ml) was added again, the mixture was stirred at 160° C. for 22 hours. Water was added with ice cooling and the precipitate was filtered. The precipitate was recrystallized from dichloromethane-methanol to give 176 g of YI1 (yield 79.6%).

Melting point: 203.5°–207.8° C.

$^1$H NMR (CDCl$_3$): 7.28–7.41 (m, 5H), 7.42–7.53 (m, 5H)

IR (KBr): 690, 748, 755, 950, 978, 1022, 1058, 1448, 1503, 1602, 1752, 3040, 3430 (cm$^{-1}$)

Elemental analysis Calcd. (%) C: 75.94, H: 4.67, N: 5.90 Found (%) C: 75.76, H: 4.76, N: 5.91

(2) YI1 (0.50 g, 2.1 mmol) obtained above was dissolved in chloroform (20 ml) and chlorosulfonic acid (0.42 ml, 6.3 mmol) was added at room temperature, and the mixture was stirred under reflux for 10 minutes. Methyl ethyl ketone and brine were added and the mixture was partitioned between them. The organic layer was washed twice with water and dried, followed by washing in turn with a small amount of dichloromethane, water and methanol to give 0.18 g of YI2 (yield 26%).

Melting point: 232.5°–234.0° C.

$^1$H NMR (d$^6$DMSO): 7.33 (d, 2H, J=8Hz), 7.41–7.53 (m, 5H), 7.56 (d, 2H, J=8 Hz)

IR (Nujor): 560, 596, 730, 756, 840, 1056, 1162, 1175, 1194, 1409, 1430, 1590, 1746, 3090, 3180 (cm$^{-1}$)

Elemental analysis: C$_{15}$H$_{10}$ClNO$_4$S.0.2H$_2$O.0.1HCl Calcd. (%) C: 52.52, H: 3.09, Cl: 11.37, N: 4.08, S: 9.35 Found (%) C: 52.15, H: 3.12, Cl: 11.70, N: 4.09, S: 9.05

(3) YI2 (200 mg, 0.60 mmol) obtained above was dissolved in tetrahydrofuran (20 ml) and N-methylpiperazine (0.08 ml, 0.72 mmol) was added under ice cooling, and the mixture was stirred at 0° C. for 4 hours. The solvent was distilled off and the residue was recrystallized from dichloromethane-tetrahydrofuran to give 129 mg of the titled compound 0037 (yield 54%).

Melting point: 270.0°–271.0 ° C.

$^1$H NMR (d$^6$DMSO): 2.13 (s, 3H), 2.33 (m, 4H), 2.88 (m, 4H), 7.54 (m, 5H), 7.56 (d, 2H, J=9 Hz), 7.68 (d, 2H, J=9 Hz)

IR (Nujor): 590, 612, 704, 720, 743, 755, 778, 952, 1051, 1101, 1150, 1159, 1172, 1286, 1333, 1595, 1758, 2660, 2720 cm$^{-1}$ Elemental analysis: C$_{20}$H$_{21}$N$_3$O$_4$S.0.4H$_2$O Calcd. (%) C: 59.07, H: 5.40, N: 10.33, S: 7.88 Found (%) C: 59.24, H: 5.50, N: 10.21, S: 7.50

EXAMPLES 2 TO 14

According to the method similar to that described in Example 1, the reaction was conducted to give the compounds listed in the following table.

TABLE 1

[Structure: 4-X-phenyl and phenyl substituted oxazolone (O-C(=O)-NH ring)]

| Example No. | Substituent X: | Melting point | IR (cm⁻¹) |
|---|---|---|---|
| 2 (0008) | SO₂NHNH₂ | dp. 155–178° C. | (Nujol) 567, 602, 747, 839, 1023, 1058, 1171, 1336, 1601, 1737, 3150, 3290, 3380, 3560 |
| 3 (0013) | SO₂—N(piperazine)NH | mp. 241–243° C. | (Nujol) 594, 610, 748, 922, 937, 1169, 1320, 1345, 1598, 1765, 2720, 3340 |
| 4 (0014) | SO₂NHN(piperidine) | dp. 185–195° C. | (Nujol) 556, 609, 693, 732, 751, 1054, 1162, 1599, 1750, 2650, 3200 |
| 5 (0015) | SO₂NH—N(triazole) | dp. 240–243° C. | (Nujol) 556, 628, 739, 755, 1055, 1170, 1596, 1752, 3080 |
| 6 (0016) | SO₂NH—N(piperazine)NCH₃ | dp. 180–188° C. | (Nujol) 570, 598, 732, 754, 830, 1055, 1163, 1280, 1380, 1600, 1755, 3150 |
| 7 (0017) | SO₂NHCH₂CH₂—N(piperazine)NCH₃ | dp. 180–194° C. | (Nujol) 512, 609, 770, 1050, 1102, 1161, 1319, 1592, 1658, 3400 |
| 8 (0035) | SO₂NH—(piperidine)N—CH₂—phenyl | mp. 259–262° C. | (Nujol) 561, 629, 696, 736, 752, 1070, 1157, 1597, 1750, 3260 |

TABLE 2

| Example No. | Substituent X: | Melting point | IR (cm⁻¹) |
|---|---|---|---|
| 9 (0036) | SO₂NHN(morpholine)O | dp. 210–217° C. | (Nujol) 560, 625, 735, 755, 839, 859, 1055, 1100, 1163, 1600, 1749, 3170 |
| 10 (0038) | —SO₂NH(CH₂)₂—N(morpholine)O | mp. 104–131° C. | (Nujol) 603, 735, 778, 927, 1114, 1158, 1600, 1780, 3110, 3630 |
| 11 (0063) | SO₂NH—phenyl—CONH₂ | dp. 257–287° C. | (Nujol) 567, 599, 757, 910, 1164, 1377, 1600, 1733, 3150, 3380 |

TABLE 2-continued

| Example No. | Substituent X: | Melting point | IR (cm$^{-1}$) |
|---|---|---|---|
| 12 (0064) | SO$_2$N(cyclohexyl) | mp. 248–250° C. | (Nujol) 579, 597, 745, 925, 1056, 1158, 1598, 1752, 3090 |
| 13 (0074) | SO$_2$NH—C$_6$H$_4$—COOH | 300° C.< | (Nujol) 558, 596, 698, 732, 906, 1152, 1245, 1607, 1730, 3180 |
| 14 (0010) | —SO$_3$H | 300° C.< | (Nujol) 570, 635, 738, 1009, 1046, 1130, 1202, 1220, 1603, 1770, 3150, 3280 |

EXAMPLES 15 TO 18

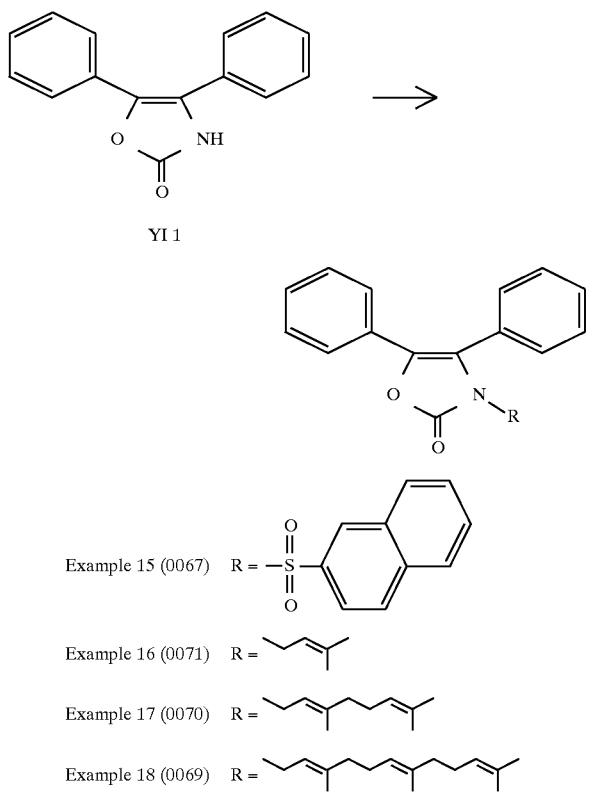

EXAMPLE 15

Compound (0067) wherein R is 2-naphthalenesulfonyl

Sodium hydride (100 mg, about 2.5 mmol) washed with a small amount of n-hexane was suspended in benzene (2 ml) and YI1 (200 mg, 0.84 mmol) produced in Example 1 (1) was added to the suspension at room temperature, and the mixture was stirred for 20 minutes. 2-Naphthalenesulfonyl chloride (950 mg, 4.2 mmol) was dissolved in benzene (3 ml) and the resulting solution was added thereto at room temperature, followed by stirring for one hour and half. Ethyl acetate and water were added and the mixture was partitioned between them. Then, the organic layer was dried and the resulting solid was recrystallized from ethyl acetate/dichloromethane to give 152 mg of compound 0067 (yield 42.2%).

Melting point: 205.5°–207.5° C.

$^1$H NMR (CDCl$_3$): 7.06–7.24 (m, 5H), 7.36–7.76 (m, 7H), 7.81–8.04 (m, 4H), 8.41 (d, 1H, J=2 Hz)

IR (Nujor): 543, 577, 653, 700, 750, 766, 770, 808, 1062, 1073, 1179, 1230, 1250, 1385, 1790 (cm$^{-1}$) Elemental analysis (%): C$_{25}$H$_{17}$NO$_4$S.0.2H$_2$O Calcd. (%) C: 69.66, H: 4.07, N: 3.25, S: 7.44 Found (%) C: 69.56, H: 4.12, N: 3.26, S: 7.33

EXAMPLE 16

Compound (0071) wherein R is prenyl

According to the method similar to that described in Example 15, the reaction was conducted to give compound 0071.

Melting point: 91.0°–92.0° C.

$^1$H NMR (CDCl$_3$): 1.31 (s, 3H), 1.61 (s, 3H), 4.08 (d, 2H, J=7 Hz), 5.07 (t, 1H, J=7 Hz), 7.14–7.30 (m, 5H), 7.35–7.46 (m, 2H), 7.47–7.56 (m, 3H)

IR (Nujor): 696, 750, 762, 770, 1056, 1745 (cm$^{-1}$)

Elemental analysis: Calcd. (%) C: 78.66, H: 6.27, N: 4.59 Found (%) C: 78.78, H: 6.43, N, 4.61

EXAMPLE 17

Compound (0070) wherein R is geranyl

According to the method similar to that described in Example 15, the reaction was conducted to give compound 0070.

Colorless liquid $^1$H NMR (CDCl$_3$): 1.29 (s, 3H), 1.57 (s, 3H), 1.66 (s, 3H), 1.85–2.10 (m, 4H), 4.10 (d, 1H, J=7), 4.90–5.13 (m, 2H), 7.15–7.30 (m, 5H), 7.36–7.54 (m, 5H)

Elemental analysis (%): C$_{25}$H$_{27}$NO$_2$.0.4H$_2$O O Calcd. (%) C: 78.87, H: 7.36, N: 3.68 Found (%) C: 78.74, H: 7.31, N, 3.76

EXAMPLE 18

Compound (0069) wherein R is farnesyl

According to the method similar to that described in Example 15, the reaction was conducted to give compound 0069.

Colorless liquid $^1$H NMR (CDCl$_3$): 1.30 (s, 3H), 1.52–1.63 (m, 9H), 1.67 (s, 3H), 1.81–2.17 (m, 12H), 4.09 (d, 2H, J=7), 4.96–5.16 (m, 4H), 7.14–7.30 (m, 5H), 7.35–7.55 (m, 5H)

Rf value: 0.2 (ethyl acetate/n-hexane=1/6)

EXAMPLES 19 TO 26

According to the method similar to that described in Example 15, the reaction was conducted to give the compounds listed in the following table.

TABLE 3

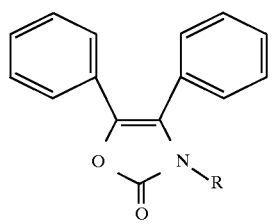

| Example No. | Substituent: R | Melting point | IR(cm$^{-1}$) |
|---|---|---|---|
| 19 (0066) | | mp. 188–189° C. | (Nujol)562, 591, 677, 700, 750, 1060, 1172, 1192, 1230, 1788 |
| 20 (0068) | —SO$_2$(CH$_2$)$_5$CH$_3$ | mp. 154–156° C. | (Nujol)555, 690, 700, 752, 772, 1068, 1165, 1235, 1785 |
| 21 (0072) | Geranyl geranyl | Liquid | |
| 22 (0116) | CPh$_3$ | dp. 156–164° C. | (Nujol)687, 695, 738, 753, 1060, 1253, 1291, 1492, 1598, 1763 |
| 23 (0117) | CH—Ph$_2$ | mp. 195–202° C. | (Nujol)695, 731, 750, 1064, 1258, 1335, 1761 |

TABLE 4

| Example No. | Substituent | Melting point | IR(cm$^{-1}$) |
|---|---|---|---|
| 24 (0040) | X = —C$_6$H$_4$—SO$_2$—N(piperidine)<br>Y = —Ph<br>R = —CH$_2$—Ph | mp. 60–70° C. | (Nijol) 580, 597, 700, 741, 929, 1050, 1164, 1341, 1382, 1598, 1762 |
| 25 (0065) | X = —C$_6$H$_4$—SO$_2$—N(piperazine)N—CH$_3$ ·HCl<br>Y = —Ph<br>R = —CH$_2$—Ph | mp. 225–223° C. | (Nijol) 596, 611, 697, 750, 942, 1166, 1190, 1377, 1751, 2220, 3380, 3590 |

TABLE 4-continued

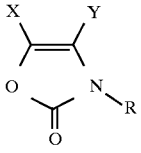

| Example No. | Substituent | Melting point | IR(cm$^{-1}$) |
|---|---|---|---|
| 26 (0118) | X = [phenyl]<br>Y = H<br>R = —CH$_2$—[quinolinyl]·HCl | mp. 152–179° C. | (Nijol) 705, 742, 1100, 1149, 1212, 1411, 1609, 1649, 1745, 2430, 3075 |

EXAMPLES 27 TO 28

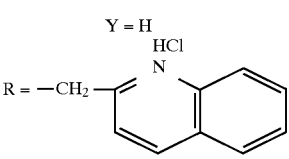 → 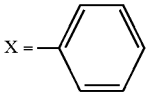

Y18

Example 27 (0095) R$^1$ = 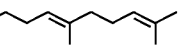

Example 28 (0097) R$^1$ = 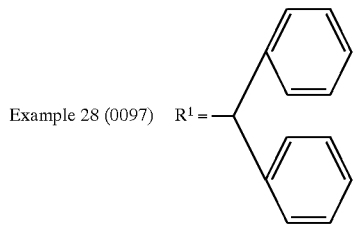

According to the method similar to that described in Example 15, the synthesis was conducted using Y18 described in J. Org. Chem., 49, 2231 (1984) as a starting material, and the following compounds were obtained.

EXAMPLES 27

Compound (0095) wherein R$^1$ is geranyl

Melting point: 56.0°–56.5° C.

$^1$H NMR (CDCl$_3$): 1.61 (s, 3H), 1.68 (s, 3H), 1.77 (s, 3H), 2.10 (brs, 4H), 4.23 (d, 2H, J=7 Hz), 5.07 (m, 1H), 5.30 (t, 1H, J=7 Hz), 6.69 (s, 1H), 7.22–7.51 (m, 5H)

IR (Nujor): 684, 733, 1020, 1040, 1182, 1731, 3130 (cm$^-$)

Elemental analysis (%): C$_{19}$H$_{23}$NO$_2$.0.1H$_2$O Calcd. (%) C: 76.27, H: 7.82, N: 4.68 Found (%) C: 76.26, H: 7.63, N: 4.86

EXAMPLES 28

Compound (0097) wherein R$^1$ is benzhydryl

Melting point: 174°–183° C.

$^1$H NMR (CDCl$_3$): 6.54 (s, 1H), 6.61 (s, 1H), 7.19–7.49 (m, 15H)

IR (Nujor): 681, 688, 717, 735, 750, 1085, 1166, 1213, 1370, 1492, 1750, 3030, 3060 cm$^{-1}$ Elemental analysis (%): Calcd. (%) C: 80.71, H, 5.23, N, 4.28 Found (%) C: 81.03, H, 5.63, N: 4.03

EXAMPLES 29 TO 32

According to the method similar to that described in Example 27, the reaction was conducted to give the compounds listed in the following table.

TABLE 5

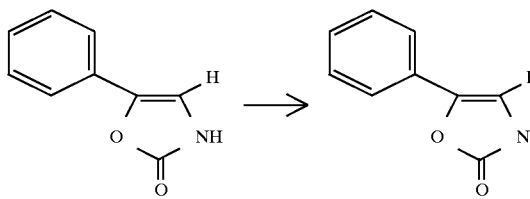

| Example No. | Substituent: R | Melting point ( ) | IR(cm$^{-1}$) |
|---|---|---|---|
| 29 (0094) | [isobutenyl] | 88–89 | (Nijol) 687, 740, 1023, 1042, 1180, 1383, 1400, 1738, 3135 |
| 30 (0096) | —CH$_2$CH$_2$—[phenyl] | 138–140 | (Nijol) 688, 703, 745, 1018, 1180, 1398, 1440, 1745, 3130 |
| 31 (0115) | Tr | 143–162 | (Nijol) 702, 740, 759, 1150, 1240, 1496, 1775 |
| 32 (0119) | —CH$_2$—[naphthyl] | 149–152 | (Nijol) 691, 744, 775, 1019, 1095, 1197, 1403, 1742, 3115 |

EXAMPLES 33 TO 36

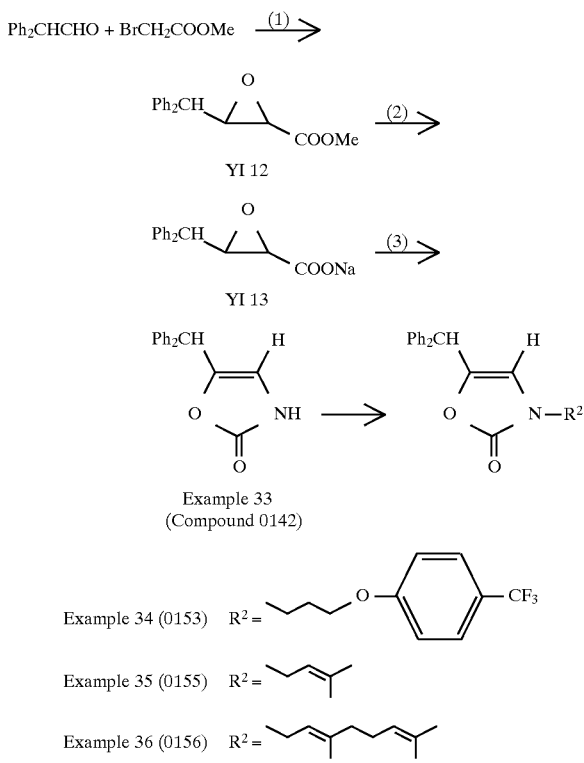

EXAMPLE 33
Compound 0142

(1) Diisopropylamine (2.79 ml, 19.9 mmol) was dissolved in THF (30 ml) and butyl lithium (12.4 ml, 19.9 mmol) was slowly added at −65° C., and the mixture was stirred under ice cooling for 25 minutes. The LDA solution prepared above was slowly added at −78° C. to a solution of diphenylacetaldehyde (3.00 g, 15.3 mmol), methyl bromoacetate (1.74 ml, 18.4 mmol) in THF (30 ml). After stirring at −78° C. for 45 minutes, the mixture was concentrated under reduced pressure and partitioned between ethyl acetate and water. The organic layer was dried over magnesium sulfate and concentrated under reduced pressure and the residue was purified by silica gel column chromatography to give 2.68 g of yellow liquid YI12.

(2) YI12 (9.46 g, 36.2 mmol) obtained above was dissolved in methanol (200 ml), to which were added a 28 wt % NaOMe methanol solution (7.4 ml, 36 mmol) and H$_2$O (0.65 ml, 36 mmol) at room temperature, and the mixture was allowed to stand overnight. The solvent was evaporated to dryness to give 10.7 g of a white solid (YI13).

(3) YI13 (1.00 g, 3.6 mmol) obtained above was dissolved in THF (30 ml) and oxalyl chloride (1.1 ml, 13 mmol) and two drops of DMF were added in turn at −20° C., and the mixture was stirred at room temperature for one hour. The reaction mixture was concentrated under reduced pressure and flushed twice with THF. Then, THF (30 ml) and trimethylsilyl azide (2.4 ml, 18 mmol) were added at room temperature and the mixture was refluxed at 85° C. for 3 hours. The reaction solution was concentrated under reduced pressure and partitioned between a dichloromethane solution containing 10% methanol and water, and the organic layer was washed with water and concentrated under reduced pressure. The residue was purified by silica gel column chromatography and recrystallized from dichloromethane/ether to give 63 mg of compound 0142 (yield 4.6%).

Melting point: 196.0°–202.5° C.
$^1$H NMR (CDCl$_3$): 5.16 (s, 1H), 6.02 (t, 1H, J=2 Hz), 7.16–7.38 (m, 10H)
IR (Nujor): 703, 736, 759, 800, 954, 1232, 1256, 1494, 1730, 1740, 3130, 3150, 3200 (cm$^{-1}$)
Elemental analysis: Calcd. (%) C: 76.48, H: 5.21, N: 5.57 Found (%) C: 76.20, H: 5.39, N: 5.63

EXAMPLE 34
Compound (0153) wherein R$^2$ is 3-(p-trifluoromethylphenoxy)propyl Compound 0142 (70 mg, 0.28 mmol) obtained in Example 33 was dissolved in DMF (2 ml) and about 60% sodium hydride (12 mg, 0.31 mmol) and 3-(p-trifluoromethylphenoxy)propyl bromide (160 mg) were added at room temperature, and the mixture was stirred for 30 minutes. Ethyl acetate and water were added and the mixture was partitioned between them, and the organic layer was washed with water and then concentrated under reduced pressure. The residue was purified by silica gel column chromatography and recrystallized from ether/n-hexane to give 68 mg of compound 0153 (yield 54%).

Melting point:: 99.5°–101.5° C.
$^1$H NMR (CDCl$_3$): 2.16 (m, 2H), 3.74 (t, 2H, J=7 Hz), 4.02 (t, 2H, J=6 Hz), 5.12 (s, 1H), 5.90 (d, 1H, J=1Hz), 6.88 (d, 2H, J=9 Hz), 7.10–7.34 (m, 10H), 7.52 (d, 2H, J=9 Hz)
IR (Nujor): 639, 702, 726, 739, 749, 842, 967, 1069, 1084, 1112, 1121, 1155, 1165, 1178, 1262, 1315, 1321, 1330, 1407, 1498, 1521, 1618, 1769, 3035, 3070, 3150 (cm$^{-1}$)
Elemental analysis: Calcd. (%) C: 68.87, H: 4.89, F: 12.57, N: 3.09 Found (%) C: 68.57, H: 5.05, F: 12.32, N: 3.06

EXAMPLE 35
Compound (0155) wherein R$^2$ is prenyl
The reaction is conducted in the manner similar to that described in Example 34.
Liquid (yellow)
$^1$H NMR (CDCl$_3$): 1.73 (s, 3H), 1.74 (s, 03H), 4.09 (d, 2H, J=7), 5.14 (s, 1H), 5.20 (t, 1H, J=7), 5.91 (d, 1H, J=1), 7.17–7.37 (m, 10H)
IR (film): 685, 702, 723, 745, 751, 965, 1025, 1066, 1070, 1146, 1161, 1193, 1355, 1368, 1381, 1395, 1451, 1498, 1601, 1753, 2940, 2985, 3040 (cm$^{-1}$)
Elemental analysis: C$_{21}$H$_{21}$NO$_2$.0.2H$_2$O Calcd. (%) C: 78.09, H: 6.68, N: 4.34 Found (%) C: 77.89, H: 7.01, N: 4.58

EXAMPLE 36
Compound (0156) wherein R$^2$ is geranyl
The reaction is conducted in the manner similar to that described in Example 34.
Yellow liquid
$^1$H NMR: (CDCl$_3$) 1.57 (s, 3H), 1.65 (s, 3H), 1.67 (s, 3H), 2.04 (brs, 4H), 4.12 (d, 2H, J=7), 5.03 (m, 1H), 5.14 (s, 1H), 5.20 (t, 1H, J=7), 5.92 (d, 1H, J=1), 7.16–7.38 (m, 10H)
IR: (Nujor) 701, 717, 747, 965, 1083, 1094, 1160, 1378, 1405, 1437, 1498, 1603, 1663, 1738, 3035, 3070, 3150 (cm$^{-1}$)
Elemental analysis: C$_{26}$H$_{29}$NO$_2$.0.1H$_2$O Calcd. (%) C: 80.21, H: 7.56, N: 3.60 Found (%) C: 80.27, H: 7.68, N: 3.46

EXAMPLES 37 TO 39
According to the method similar to that described in Example 34, the reaction was conducted to give the compounds listed in the following table.

TABLE 6

| Example No. | Substituent | Melting point (°C.) | IR(cm$^{-1}$) |
|---|---|---|---|
| 37 (0143) | R$^2$ = —CH$_2$—C$_6$H$_5$ | Liquid | (film) 697, 742, 965, 1065, 1080, 1152, 1396, 1451, 1495, 1754, 3040 |
| 38 (0154) | R$^2$ = PMZ | 179–180 | (Nijol) 700, 747, 1050, 1166, 1731, 1229, 1250, 1270, 1384, 1513, 1612, 1825 |
| 39 (0157) | R$^2$ = —CH$_2$—naphthyl | 127–129 | (Nijol) 700, 710, 742, 825, 1053, 1139, 1410, 1492, 1770, 3130 |

Reference Example 1

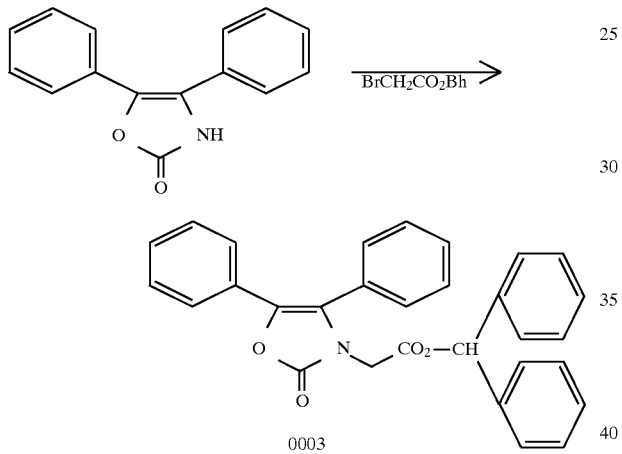

EXAMPLES 40 TO 43

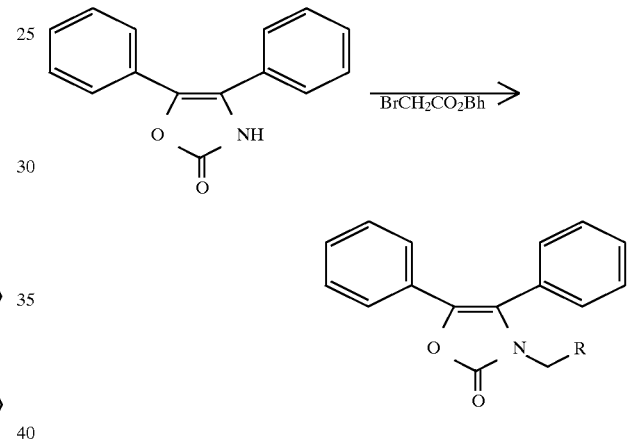

The compound YI1 (500 mg, 2.1 mmol) produced in Example 1 (1) and benzhydryl bromoacetate (723 mg, 2.4 mmol) were dissolved in DMF (3 ml), and then NaH (60% in oil) (100 mg, 2.5 mmol) was added in several portions under a N$_2$ stream with ice cooling. After the addition, the mixture was warmed to room temperature and stirred for 2 hours. The reaction solution was poured into ice water and extracted with AcOEt. The organic layer was washed in turn with water and brine, and then dried over Na$_2$SO$_4$, and concentrated under reduced pressure to give 994 mg of a light brown syrup-like substance. The substance was subjected to silica gel column chromatography and eluted with AcOEt/hexane (1:4), then concentrated under reduced pressure to give 760 mg of a colorless syrup-like substance. The substance was recrystallized from AcOEt/hexane (1:3) to give 544 mg of a white columnar crystal (56%). 0003: —CH$_2$CO$_2$Bh Yield 56%

Melting point: 162°–164° C. C$_{30}$H$_{23}$NO$_4$ (461, 492)

Elemental analysis Calcd.: 78.07, 5.02, 3.04 Found: 77.95, 5.20, 3.07

Mass (M/e) M$^+$ 461, 167 (base peak)

IR (KBr): 1760, 1744, 1496, 1444, 1406, 1370, 1198, 1059, 748, 700

NMR (CDCl$_3$) δ 4.30 (2H, s), 6.87 (1H, s), 7.15~7.50 (20H, m)

According to the method similar to that described in Reference Example 1 except for reacting under the condition indicated in the following table, the following compounds were produced.

TABLE 7

| Example No. (Compound No.) | Reagent | Reaction condition |
|---|---|---|
| 40 (0044) | Br—CH$_2$CH$_2$CH$_2$CH$_3$ | at room temperature overnight |
| 41 (0086) | Cl—CH$_2$—CH=CH—(2-thienyl)—Cl | at room temperature overnight |
| 42 (0099) | Cl—CH$_2$—O—CH$_2$—C$_6$H$_5$ | at 0° C. for 6 hours |
| 43 (0109) | Cl—CH$_2$—(3,5-dimethylisoxazol-4-yl) | at room temperature overnight |

EXAMPLE 40

Compound (0044) wherein R is n-butyl
Yield: 29%
Melting point: 62°–64° C.
IR (KBr): 1745, 1501, 1361, 1233, 1055, 770, 705
Mass (M/e)M⁺ 293
NMR (CDCl$_3$) δ 0.79 (3H, t), 1.10~1.30 (2H, m), 1.38~1.55 (2H, m), 3.47 (2H, t)

EXAMPLE 41

Compound (0086) wherein R is a group represented by the formula:

Yield: 53.9%
Melting point: 99°–101° C. C$_{20}$H$_{14}$NO$_2$SCl (367, 843)
Elemental analysis Calcd.: 65.30, 3.84, 3.81, 8.72, 9.64 Found: 65.38, 3.85, 3.85, 8.59, 9.58
IR (KBr) 1750, 1443, 1424, 1335, 1054, 998, 752, 702
Mass (M/e) M⁺ 367, 131 (base peak)
NMR (CDCl$_3$) δ 4.70 (2H,s), 6.46 (1H,d, 3.8 Hz), 6.66 (1H,d, 3.6 Hz), 7.15~7.30 (5H,m), 7.30~7.45 (2H,m), 7.45~7.60 (3H, m)

EXAMPLE 42

Compound (0099) wherein R is a group represented by the formula:

Yield: 41.2%
Melting point: 85°–87° C. C$_{23}$H$_{19}$NO$_3$ (357, 39)
Elemental analysis: Calcd. 77.29, 5.36, 3.92 Found 77.33, 5.36, 3.98
IR (KBr) 1764, 1604, 1502, 1458, 1346, 1264, 1075, 756, 700
Mass(M/e) M⁺ 357 91 (base peak)
NMR (CDCl$_3$) δ 4.66 (2H, s), 4.99 (2H, s), 7.18~7.40 (10H, m), 7.50 (5H, s)

EXAMPLE 43

Compound (0109) wherein R is a group represented by the formula:

Yield: 77.2%
Melting point: 91°–93° C. C$_{21}$H$_{18}$N$_2$O$_3$ (346, 37)
Elemental analysis Calcd.: 72.37, 5.29, 8.03 Found: (¹⁄₁₀ H$_2$O), 72.44, 5.27, 8.05
IR (KBr) cm⁻¹ 1752, 1601, 1498, 1445, 1384, 1340, 1250, 1204, 1051, 768, 704
Mass(M/e)[M+H]⁺ 347 (base peak)
NMR (CDCl$_3$) δ 1.84 (3H, s), 1.96 (3H, s), 4.51 (2H, s), 7.15, 7.30 (6H, m), 7.45~7.56 (4H, m)

EXAMPLES 44 TO 49

According to the method similar to that described in Reference Example 1, the reaction was conducted to give the compounds listed in the following table.

TABLE 8

| Example No. | Substituent R: | Melting point(°C.) | IR(cm⁻¹)KBr |
|---|---|---|---|
| 44 (0033) | —CH$_2$CH$_2$N(CH$_3$)$_2$ | 81–83 | 1755, 1446, 1380, 1023, 751, 700 |
| 45 (0042) | —CH$_2$CO—⟨biphenyl⟩ | 161–163 | 1752, 1689, 1446, 1387, 1237, 759, 698 |
| 46 (0045) | —CH$_2$—⟨quinoline⟩ | 171–173 | 1746, 1601, 1502, 1380, 1057, 768, 702 |
| 47 (0049) | —CH$_2$—⟨C$_6$H$_4$⟩—COOCH$_3$ | 110–112 | 1756, 1716, 1283, 1111, 751, 696 |

TABLE 8-continued

[Structure: diphenyl compound with O-C(=O)-N-R group]

| Example No. | Substituent R: | Melting point (°C) | IR(cm⁻¹)KBr |
|---|---|---|---|
| 48 (0087) | -CH₂-cyclopropyl | 125–127 | 1744, 1370, 1051, 748, 701 |
| 49 (0098) | -CH₂-C₆H₄-NO₂ | Foam-like | 1755, 1602, 1518, 1342, 1054, 758, 701 |

EXAMPLE 50

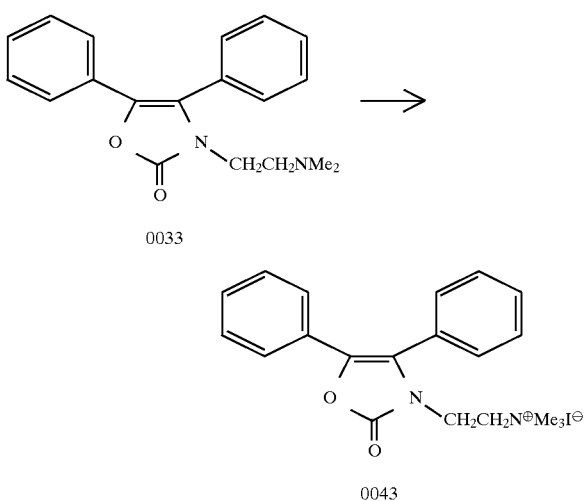

0033 → 0043

The compound 0033 (100 mg, 0.32 mmol) produced in Example 44 was dissolved in EtOH (2 ml) and a solution of MeI (0.46 g, 3.2 mol) in EtOH (1 ml) was added at room temperature, and the mixture was allowed to stand overnight. A crystal precipitated was filtered and washed with cooled EtOH to give 43.5 mg of a colorless columnar crystal (compound 0043, 30%).

Melting point: 237°–239° C. $C_{20}H_{23}N_2O_2I$ (450.32)

Elemental analysis

Calcd.: 52.83, 5.22, 6.12, 28.15 Found: (⅕ H₂O): 52.92, 5.20, 6.17, 27.96

IR (KBr): 1745, 1448, 1378, 747

EXAMPLES 51 TO 59

[Structure: diphenyl compound with O-C(=O)-N-R group]

| Example No (Compound No.) | R |
|---|---|
| 51(0039) | -CH₂-C₆H₄-F (meta) |
| 52(0047) | -CH₂-C₆H₄-F (ortho) |
| 53(0048) | -CH₂-C₆H₄-F (para) |
| 54(0062) | -CH₂C≡CH |
| 55(0090) | -CH₂CH₂CH₂CH₂O-C₆H₅ |
| 56(0091) | -CH₂-(2-pyridyl) |

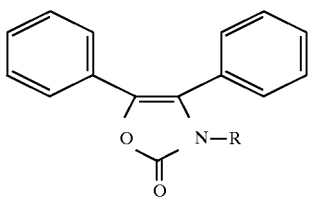

| Example No (Compound No.) | R |
|---|---|
| 57(0024) | 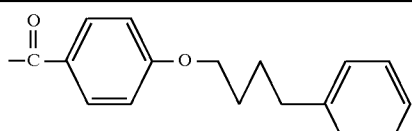 |
| 58(0056) | 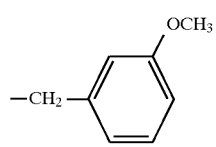 |
| 59(0057) | 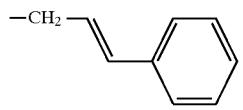 |

According to the method similar to that described in Reference Example 1 except for using a 4,5-diphenyloxazol-2-one reagent explained in the following Examples as a starting material, the above compounds were synthesized. The yield and various data are described below.

EXAMPLE 51
3-(3-Fluorobenzyl)-4,5-diphenyl-oxazol-2-one (0039)
Starting material: m-Fluorobenzyl chloride
Yield 31%, oily substance
NMR δ (CDCl$_3$) ppm: 4.65 (s, 2H), 6.68 (d, J=9.4 Hz, 1H), 6.80 (d, J=7.8 Hz, 1H), 6.92 (dd, J=8.2 and 8.2 Hz, 1H), 7.1~7.3 (m, 8H), 7.4~7.5 (m, 3H)

EXAMPLE 52
3-(2-Fluorobenzyl)-4,5-diphenyl-oxazol-2-one (0047)
Starting material: o-Fluorobenzyl chloride
Yield 48%, oily substance
NMR (CDCl$_3$) ppm: 4.75 (s, 2H), 6.8~7.3 (m, 11H), 7.3~7.5 (m, 3H)

EXAMPLE 53
3-(4-Fluorobenzyl)-4,5-diphenyl-oxazol-2-one (0048)
Starting material: p-Fluorobenzyl chloride
Yield 65%
Melting point: 84° to 85° C., colorless crystal
NMR δ (CDCl$_3$) ppm: 4.63 (s, 2H), 6.8~7.0 (m, 4H), 7.1~7.3 (m, 7H), 7.4~7.6 (m, 3H)

EXAMPLE 54
Compound 0062
4,5-Diphenyloxazol-2-one (500 mg, 2.11 mmol) was dissolved in DMF (4 ml) and sodium hydride (153 mg, 2.55 mmol) was added under nitrogen and with ice cooling over 20 minutes. After stirring for 20 minutes, propargyl bromide (210 μl, 2.79 mmol) was added. After stirring for 15 minutes with ice cooling and stirring at room temperature for 2 hours, water (20 ml) was added and the mixture was extracted with ethyl acetate. The extract was washed in turn with water and brine, dried over magnesium sulfate, and concentrated under reduced pressure. The residue was purified by silica gel column chromatography to give 3-(2-propynyl)-4,5-diphenyl-oxazol-2-one.
Yield 45%
Melting point: 136°~137° C. Colorless crystal
NMR δ (CDCl$_3$) ppm: 2.26 (t, J=2.6 Hz, 1H), 4.23 (m, J=2.6 Hz, 2H), 7.2~7.3 (m, 5H), 7.5~7.6 (m, 5H)

EXAMPLE 55
3-(4-Phenoxybenzyl)-4,5-diphenyl-oxazol-2-one (0090)
Starting material: 4-Phenoxybutyl bromide
Yield 50%, oily substance
NMR δ (CDCl$_3$) ppm: 1.69 (m, 4H), 3.56 (m, 2H), 3.81 (m, 2H), 6.7~7.0 (m, 3H), 7.1~7.3 (m, 7H), 7.3~7.5 (m, 5H)

EXAMPLE 56
3-(2'-Pyridylmethyl)-4,5-diphenyl-oxazol-2-one (0091)
Starting material: 2-Picolyl chloride hydrochloride
Yield 3%, oily substance
NMR δ(CDCl$_3$) ppm: 4.79 (s, 2H), 7.2~8.0 (m, 13H), 8.9 (d, J=4.6 Hz, 1H)

EXAMPLE 57
Compound 0024
4,5-Diphenyloxazol-2-one (100 mg, 0.42 mmol) was dissolved in pyridine (0.5 ml) and a solution of 4-(4'-phenyl)-butoxy-benzoyl chloride (134 mg, 0.46 mmol) in pyridine (0.5 ml) was added with ice cooling. After one hour at room temperature, the mixture was treated in conventional manner to give 225 mg of the product. The product was subjected to silica gel chromatography, and fractions eluted with hexane/EtOAc (85:15) are collected. Oily substance 95 mg
Yield: 46%
NMR δ (CDCl$_3$) ppm: 1.83 (m, 4H), 2.70 (t, J=4.8 Hz, 2H), 4.05 (t, J=4.8 Hz, 2H), 6.93 (d, J=9.0 Hz, 2H), 7.14~7.45 (m, 15H), 7.90 (d, J=9.0 Hz, 2H)

EXAMPLE 58
Compound 0056, oily substance
NMR δ (CDCl$_3$) ppm: 3.72 (s, 3H), 4.64 (s, 2H), 6.5~6.8 (m, 3H), 7.1~7.6 (m, 11H)

EXAMPLE 59
Compound 0057, melting point: 123°–124 ° C. (EtOAc)
NMR δ (CDCl$_3$): 4.26 (d, J=5.6 Hz, 2H), 6.07 (m, 1H), 6.23 (d, J=16.0 Hz, 2H), 7.20~7.6 (m, 15H).

EXAMPLES 60 TO 62

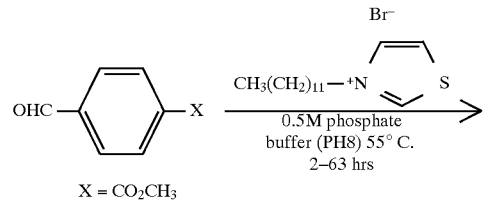

X = CO$_2$CH$_3$

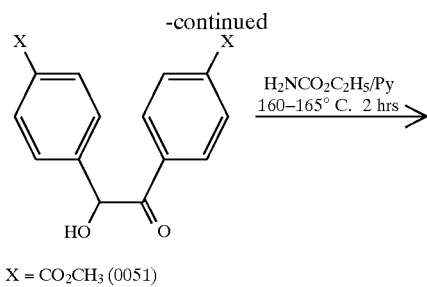

X = CO₂CH₃ (0051)

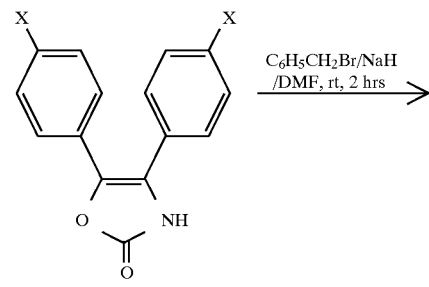

X = CO₂CH₃ [Example No. 60 (0020)]

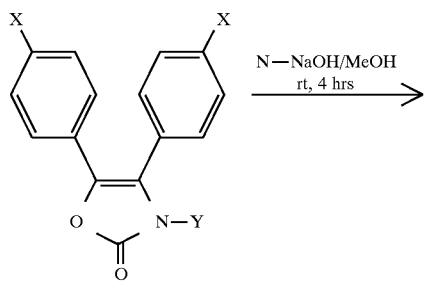

X = CO₂CH₃, Y = CH₂C₆H₅
Example No. 61 (0046)

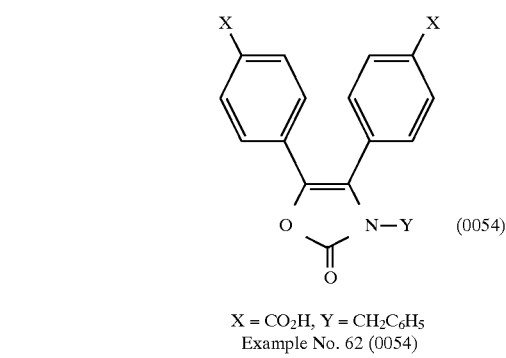

X = CO₂H, Y = CH₂C₆H₅
Example No. 62 (0054)

EXAMPLE 60
4,5-Bis-(4-methoxycarbonylphenyl)-3-oxazolin-2-one (0020)

(1) p-Methoxycarbonylbenzoin (0051)

N-Laurylthiazole bromide (2.01 g, 6 mmol) which was separately synthesized according to published literature [W. Tagaki, Bull Chemical Society Japan (1980)] was dissolved in 1 liter of a phosphate buffer (0.5 mol, pH 8). Methyl 4-formyl benzoate (9.85 g, 60 mmol) was added to the solution with stirring at room temperature and the mixture was heated at 55° C. for 6 hours. After standing at room temperature for 2 days, the crystal precipitated was filtered and dissolved in ethyl acetate. The solution was washed with water and dried over mirabilite, then filtered and concentrated. The resulting residue was recrystallized from ethyl acetate to give 7.23 g of the product (73%).

Melting point: 143°~147° C.
Elemental analysis ($C_{18}H_{16}O_6$) Calcd.: C, 65.85; H, 4.91 Found: C, 65.56; H, 5.04
IR (Nujol) cm⁻¹: 3454, 3424, 1722, 1678, 1609.
NMR (CDCl₃) δ: 3.88 (3H, s), 3.92 (3H, s), 4.54 (1H, brd, J=6.6 Hz), 6.02 (1H, brd, J=4.2 Hz), 7.40 (2H, d, J=8.4 Hz), 7.90~8.08 (6H, m).

(2) 4,5-Bis-(4-methoxycarbonylphenyl)-3-oxazolin-2-one (0020)

p-Methoxycarbonylbenzoin (2, 6.566 g, 20 mmol) obtained above was mixed with ethyl carbamate (8.91 g, 100 mmol) and dried pyridine (1.62 ml, 20 mmol) was added to the mixture. After heating at 160° C. for 2 hours under nitrogen gas, the mixture was cooled to precipitate a crystal, to which was added ether (80 ml), and the crystal was filtered and washed to give 5.87 g of the titled compound (83%).

Melting point. 255°~264° C.
Elemental analysis ($C_{19}H_{15}NO_6 \cdot \frac{1}{4} H_2O$) Calcd.: C, 63.77; H, 4.37; N, 3.91 Found: C, 63.96; H, 4.38; N, 4.24
IR (KBr) cm⁻¹: 1764, 1725, 1606
NMR (DMSO) δ: 3.84 (3H, s), 3.88 (3H, s), 6.42 (1H, brs), 7.50 (2H, d, J=8.8 Hz), 7.67 (2H, d, J=8.8 Hz), 7.92 (2H, d, J=8.8 Hz), 8.04 (2H, d, J=8.8 Hz).

EXAMPLE 61
3-Benzyl-4,5-bis-(4-methoxycarbonylphenyl)-3-oxazolin-2-one (0046)

4,5-bis-(4-methoxycarbonylphenyl)-3-oxazolin-2-one (3, 3.53 g, 10 mmol) obtained above was dissolved in dried DMF (50 ml), and benzyl bromide (3.57 ml, 30 mmol) and 60% NaH (600 mg, 15 mmol) were added with stirring at 0° C. under nitrogen gas. After stirring at room temperature for 4 hours, the reaction solution was poured into ice water and extracted with ethyl acetate. The extract was washed with water, dried, and concentrated. The resulting residue was subjected to silica gel chromatography to give 1.02 g of the titled compound (23%).

Elemental analysis ($C_{26}H_{21}NO_6$) Calcd.: C, 70.42; H, 4.77; N, 3.16 Found: C, 70.20; H, 4.91; N, 3.16
Melting point. 54°~58° C.
IR (CHCl₃) cm⁻¹: 1753, 1718, 1608.
NMR (CDCl₃) δ: 3.07 (3H, s), 3.98 (3H, s), 4.69 (2H, s), 6.95~7.00 (2H, m), 7.22~7.32 (7H, m), 7.87 (2H, d, J=8.4 Hz), 8.10 (2H, d, J=8.4 Hz).

EXAMPLE 62
3-Benzyl-4,5-bis-(4-hydroxycarbonylphenyl)-3-oxazolin-2-one (0054)

3-Benzyl-4,5-bis-(4-methoxycarbonylphenyl)-3-oxazolin-2-one (4, 4.43 g, 10 mmol) obtained in Example 61 was dissolved in methanol (50 ml), and 1N-NaOH (50 ml, 50 mmol) was added with stirring and ice cooling. After stirring at room temperature for 4 hours, ice water (100 ml) and ethyl acetate (100 ml) were added and the organic layer was washed with 1N-NaOH and water. The combined aqueous layer was acidified (pH 3) with concentrated hydrochloric acid with ice cooling and extracted with ethyl acetate. The extract was washed with brine, and dried, and concentrated to give a residue (2.434 g) which was recrystallized from ether to give 2.049 g of the titled compound (49%).

Melting point: 251°~256° C.
Elemental analysis ($C_{24}H_{17}NO_6 \cdot \frac{1}{2} H_2O$) Calcd.: C, 67.92; H, 4.28; N, 3.30 Found: C, 68.08; H, 4.13; N, 3.10
IR (Nujol) cm⁻¹: 3425 (br), 2660, 2542, 1733, 1688, 1606.
NMR (CDCl₃+DMSO=7:1) δ: 4.70 (2H, s), 6.96~7.01 (2H, m), 7.23~7.36 (6H, m), 7.86 (2H, d, J=8.8 Hz), 8.08~8.12 (2H+H, d).

EXAMPLES 63 TO 64

C₆H₅CH₂Br/NaH
/DMF, room temperature, 2 hours,

Compound 0020 →

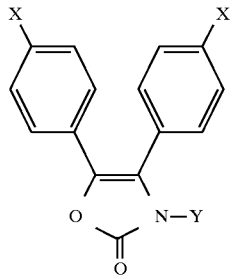

X = CO₂CH₃, Y = BOC   Example No. 63 (0023)
X = F, Y = CH₂C₆H₅   Example No. 64 (0112)

According to the method similar to that described in Example 61 except for using the compound 0020 produced in Example 60 as a starting material, the reaction was conducted to give compounds 0023 and 0112.

EXAMPLE 63

Compound 0023

Melting point: 270°~271° C.

Elemental analysis ($C_{24}H_{23}NO_8$) Calcd.: C, 63.57 H, 5.11 N, 3.09 Found: C, 63.62; H, 5.29 N, 3.00

IR (CHCl₃) cm⁻¹: 1818, 1719, 1619.

NMR CDCl₃) δ: 1.25 (9H, s), 3.88 (3H, s) 3.98 (3H, s), 7.24 (2H, d, J=8.4 Hz), 7.49 (2H, d, J=8.4 Hz), 7.88 (2H, d, J=8.4 Hz) 8.17 (2H, d, J=8.4 Hz)

EXAMPLE 64

Compound 0112

Melting point: 143°~144° C.

IR (CHCl₃) cm⁻¹; 1751, 1600

NMR (CDCl₃) δ; 4.66 (2H, s), 6.87~7.26 (13H, m).

EXAMPLE 65

4,5-Bis-(4-hydrazinocarbonylphenyl)-3-oxazolin-2-one (0021)

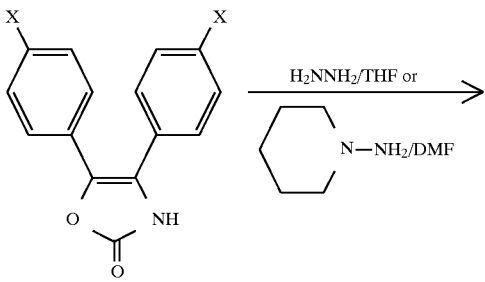

X = CO₂CH₃
(0020)

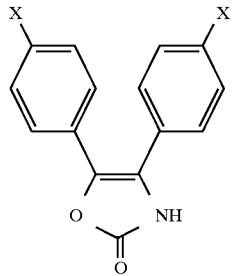

X = CONHNH₂
(0021)

4,5-Bis-(4-methoxycarbonylphenyl)-3-oxazolin-2-one (142 mg, 0.4 mmol) obtained in Example 60 was suspended in dried THF (1 ml) and hydrazine anhydride (256 μl, 40 mmol) was added, and the mixture was stirred at room temperature under nitrogen. After the solid material was dissolved in about 10 minutes, and stirring was continued for additional one hour, methylene chloride was added and the precipitate was filtered and recrystallized from DMSO/water to give 71 mg of the titled compound (8) (50%).

Melting point: >300° C.

Elemental analysis ($C_{17}H_{15}N_5O_4 \cdot \frac{1}{4} H_2O$) Calcd. C, 57.09; H, 4.37; N, 19.57 Found: C, 57.50; H, 4.43; N, 18.81.

IR (KBr) cm⁻¹: 3310, 1775, 1634, 1611.

NMR (DMSO) δ: 4.58 (4H, brs), 7.43 (2H, d, J=8.6 Hz), 7.58 (2H, d, J=8.6 Hz), 7.79 (2H, d, J=8.6 Hz), 7.90 (2H, d, J=8.6 Hz), 9.85 (2H, d, J=20 Hz), 11.51 (1H, brs).

EXAMPLES 66 TO 67

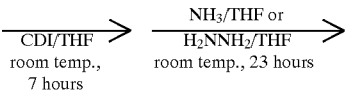

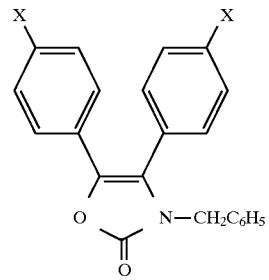

X = CONH₂   Example No. 66 (0101)
X = CONHNH₂   Example No. 67 (0102)

The compound 0054 obtained in Example 62 was used to give the above compounds 0101 and 0102.

EXAMPLE 66

Compound 0101

Melting point: 260°~267° C.

IR (Nujol) cm⁻¹; 3380, 3164, 1735, 1675, 1609

NMR (DMSO) δ; 4.70 (2H, S), 6.96~7.01 (2H, m). 7.20~7.24 (5H, m), 7.35~8.10 (10H, m)

EXAMPLE 67

Compound 0102

Melting point: 148°~153° C.

IR (Nujol) cm⁻¹; 3322, 3282, 3180, 1741, 1668, 1606, 1550.

NMR (DMSO) δ: 4.53 (4H, brs), 4.66 (2H, s), 6.97~7.02 (3H, m), 7.20~7.26 (4H, m), 7.49 (2H, d, J=8.2 Hz), 7.72 (2H, d, J=8.4 Hz), 7.92 (2H, d, J=8.2 Hz), 9.83 (2H, d, J=42.8 Hz).

EXAMPLES 68 TO 71 in Example 60 as a starting material, the reaction was conducted to give compound 0022.

Melting point: >300° C.

IR (KBr) cm$^{-1}$; 3428, 1769, 1686, 1606.

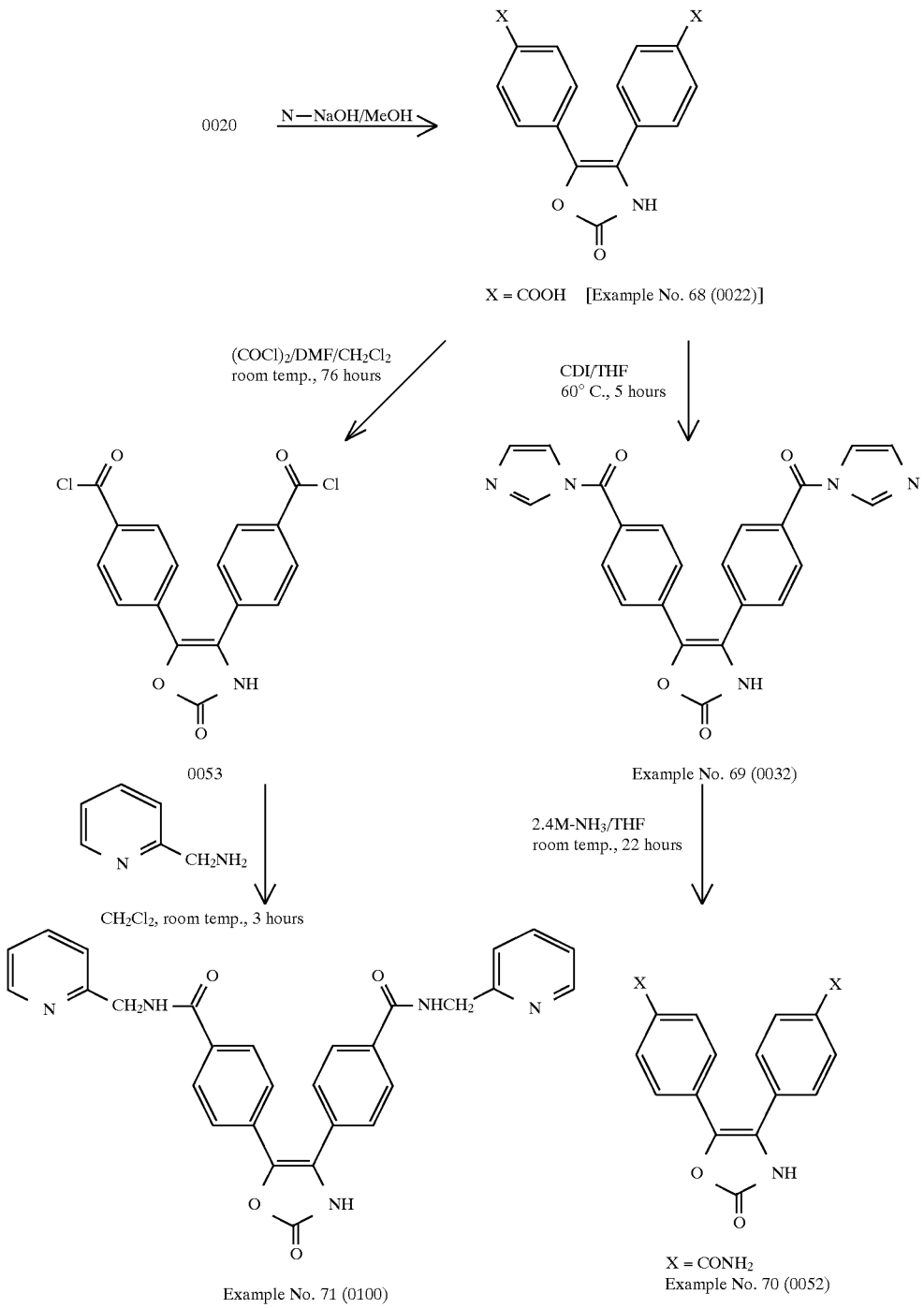

EXAMPLE 68

4,5-Bis-(4-hydroxycarbonylphenyl)-3-oxazolin-2-one (0022)

According to the method similar to that described in Example 62 except for using the compound 0020 produced NMR: (DMSO) δ; 7.52 (2H, d, J=8.6 Hz), 7.67 (2H, d, J=8.6 Hz), 7.94 (2H, d, J=8.6 Hz), 8.05 (2H, d, J=8.6 Hz), 11.64 (1H, brs).

EXAMPLE 69
4,5-Bis-(4-imidazocarbonyl phenyl)-3-oxazolin-2-one (0032)

4,5-Bis-(4-hydroxycarbonylphenyl)-3-oxazolin-2-one (compound 0022) (163 mg, 0.5 mmol) produced in Example 68 was suspended in THF (10 ml) and CDI (1,1'-carbonyldiimidazole (170 mg, 1.05 mmol) was added with stirring. After heating the mixture with stirring at 60° C. for 5 hours under nitrogen gas, precipitated solid was filtered and washed with ether, and then dried to give 170 mg of the dried titled compound (80%).

Melting point: >300° C.
Elemental analysis ($C_{23}H_{15}N_5O_4 \cdot 3H_2O$) Calcd.: C, 57.62; H, 4.42 ; N, 14.61 Found: C, 57.64 ; H, 4.12 ; N, 14.52.
IR (KBr) $cm^{-1}$: 2842, 2750, 1742, 1604, 1541.
NMR (DMSO) δ: 5.78 (1H, brs), 7.04 (4H, s), 7.49 (2H, d, J=8.6 Hz), 7.63 (2H, d, J=8.6 Hz), 7.68 (2H, s), 7.92 (2H, d, J=8.6 Hz), 8.02 (2H, d, J=8.6 Hz).

EXAMPLE 70
Compound 0052

The compound 0032 obtained in Example 69 was used to give compound 0052.

Melting point: >300° C.
Elemental analysis ($C_{17}H_{13}N_3O_4 \cdot \frac{1}{4} H_2O$) Calcd.: C, 62.28 ; H, 4.15, N, 12.82 Found: C, 61.95; H, 4.02 ; N, 12.65
IR (Nujol) $cm^{-1}$: 3434, 3188, 1758, 1655, 1609.
NMR (DMSO) δ: 7.44 (2H, d, J=8.2 Hz), 7.51 (2H, brs). 7.58 (2H, d, J=8.2 Hz), 7.85 (2H, d, J=8.2 Hz), 7.95 (2H, d, J=8.2 Hz), 8.09 (2H, brs), 11.55 (1H, brs) .

EXAMPLE 71
Compound 0100

(1) 4,5-Bis-(4-chlorocarbonylphenyl)-3-oxazolin-2-one (0053)

Oxazoline acid (12, 163 g, 0.5 mmol) obtained in Example 68 was suspended in dried dichloromethane (2 ml), and DMF (13 μl, 1/10 amount of oxalyl chloride) was added with stirring, then oxalyl chloride (131 μl, 1.5 mmol) was added thereto with stirring at 0° C. under nitrogen gas. After standing at room temperature for 76 hours, dichloromethane was added and precipitated solid was filtered and washed, and then dried to give 149 mg of the titled compound 0053 (82%).

Melting point: >300 ° C.
Elemental analysis ($C_{17}H_9NO_4Cl_2$) Calcd.: C, 56.38; H, 2.50 N, 3.84; Cl, 19.58 Found: C, 55.94H, 2.76 N, 4.14; Cl, 16.03.
IR (Nujol) $cm^{-1}$: 3170, 1766, 1725, 1686, 1597.
NMR (DMSO) δ: 7.49 (2H, d, J=8.2 Hz), 7.64 (2H, d, J=8.2 Hz), 7.92 (2H, d, J=8.2 Hz), 8.03 (2H, d, J=8.2 Hz), 11.69 (1H, s).

(2) 4,5-Bis-(4-(2-pyridino)methylaminocarbonylphenyl)-3-oxazolin-2-one (0100)

Acid chloride (0053, 72 mg, 0.2 mmol) obtained above was suspended in dichloromethane (3 ml) and 2-(aminomethyl)pyridine (82 μl, 0.8 mmol) was added at room temperature with stirring, followed by additional stirring. After 3 hours, the mixture was poured into ice water and extracted with dichloromethane/methanol (4:1). The resulting extract was washed with water, dried, and concentrated to give a residue. The resulting residue was separated with TLC ($CHCL_3:MeOH:H_2O$=32:6:0.5) and recrystallized from ether to give 37 mg of the titled compound (0100) (36%).

Melting point; 115°~118° C.
Elemental analysis ($C_{29}H_{23}N_5O_4 \cdot 2H_2O$) Calcd.: C, 64.31; H, 5.03 N, 12.93. Found: C, 64.28H, 4.99; N, 12.75.

NMR ($CDCl_3$) δ: 7.45 (4H, s), 7.15~7.50 (8H, m), 7.65~7.90 (6H, m), 7.95–8.10 (2H, m), 8.41 (2H, dd, J=18.0, 4.0 Hz), 11.14 (1H, brs)

EXAMPLES 72 TO 74

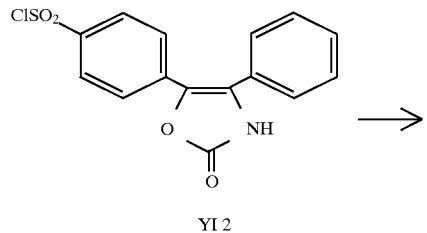

YI 2

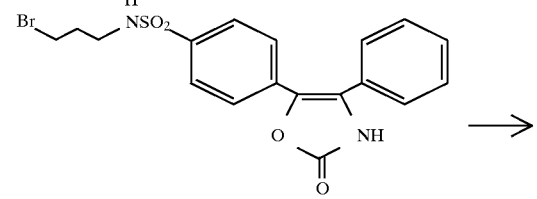

Example No. 72 (0031)

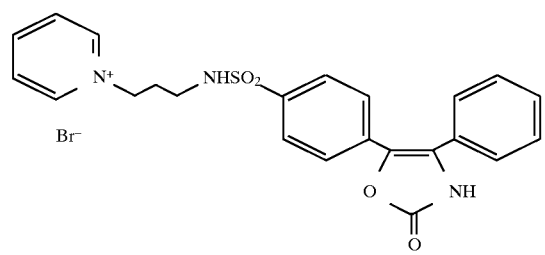

Example No. 73 (0028)

EXAMPLE 72
5-(3-Bromopropylaminosulfonylphenyl)-4-phenyl-4-oxazolin-2-one (0031)

YI2 (300 mg, 89.3 μmol) produced in Example 1 (2) was dissolved in THF (30 ml) and triethylamine (300 μl, 89.3 μM×2.4) and 3-bromopropylamine hydrobromide (235 mg, 89.3 μM×1.2) were added in turn, and the mixture was stirred at room temperature for 2 hours. The reaction solution was concentrated and partitioned between methyl ethyl ketone and water containing 2 ml of 2N hydrochloric acid. The organic layer was washed in turn with water and brine, and dried. After concentration, the crystal precipitated was recrystallized from THF and methylene chloride to give 230 mg of compound 0031 (59%).

Melting point: 232°–235° C.
$^1$H NMR (DMSO): δ 1.88 (quintet, J=6.6 Hz, 2H), 2.87 (quartet, J=6.3 Hz, 2H), 3.49 (t, J=6.4 Hz, 2H), 7.26–7.58 (m, 7H), 7.74 (d, J=8.6 Hz, 2H), 11.56 (brs, 1H)
IR (Nujol): 3240, 3170, 1740, 1600, 1164 $cm^{-1}$
Elemental analysis ($C_{18}H_{17}N_2O_4SBr \cdot 0.2H_2O$) Calcd. (%):C, 49.03; H, 3.98; N, 6.35; S, 7.27 Found (%):C, 48.88; H, 3.95; N, 6.32; S, 7.19

EXAMPLE 73
5-(3-N-pyridiniumpropylaminosulfonylphenyl)-4-phenyl-4-oxazolin-2-one bromide (0028)

The compound 0031 (200 mg, 457 μmol) was dissolved in THF (15 ml), and pyridine (888 μl, 457 μmol×24) was added at room temperature, and the mixture was stirred at 70° C. for 32 hours. The resulting precipitate was filtered and washed with THF to give 238 mg of the objective crystal product 0028 (100%).

Melting point: 185°–188° C. (with decomposition)
¹H-NMR (DMSO): δ 2.07 (quintet, J=7.0 Hz, 2H), 2.79 (quartet, J=6.0 Hz, 2H), 4.63 (t, J=7.2 Hz, 2H), 7.48–7.59 (m, 7H), 7.73 (d, J=8.8 Hz, 2H), 7.80 (t, J=5.6 Hz, 1H), 8.16 (t, J=7.1 Hz, 2H), 8.61 Hz(t, J=7.8 Hz, 1H), 9.01 (d, J=4.0 Hz, 2H)
IR (Nujol): 3000, 1753, 1630, 1598, 1483, 1327, 1156 cm⁻¹
Element analysis (C₂₃H₂₂BrN₃O₄S.0.3H₂O) Calcd. (%): C, 52.94; H, 4.37; N, 8.05; S, 5.86; Br, 15.31 Found (%): C, 53.01; H, 4.60; N, 7.75; S, 5.86; Br, 15.06

EXAMPLE 74
5-(4-bromopropyloxysulfonyl)phenyl-4-phenyloxazolin-2-one (compound 0041)

According to the method similar to that described in Example 72 except for using n-BuLi in place of triethylamine and reacting 3-bromopropanol with YI-2, the reaction was conducted to give the titled compound 0041.

Melting point: 167°–169° C.
IR (Nujol): 3190, 3020, 1760, 1750, 1728, 1602, 1185, 985, 922, 614 cm⁻¹.

EXAMPLE 75
3-Benzyl-5-phenyl-4-oxazolin-2-one (compound 0073)

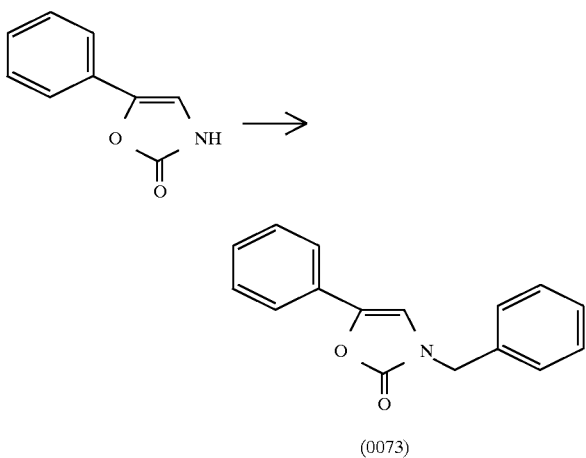

(0073)

The compound described in published literature [J. Org. Chem., 49, 2231 (1984)], 5-phenyl-4-oxazolin-2-one, was benzylated to give the titled compound 0073.

Melting point: 158°–160° C.
¹H NMR (CDCl₃): δ 4.80 (s, 2H), 6.63 (s, 1H), 7.21–7.49 (m, 10H)
IR (Nujol): 1743, 1496 cm⁻¹
Elemental analysis (%): C₁₆H₁₃NO₂.0.3H₂O Calcd.:C, 74.87; H, 5.34; N, 5.46 Found: C, 74.64; H, 5.10; N, 5.45

EXAMPLES 76 TO 77

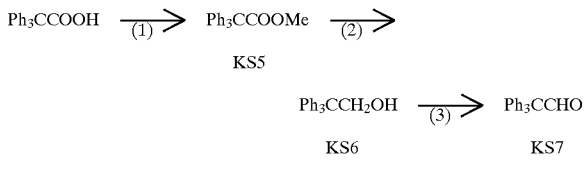

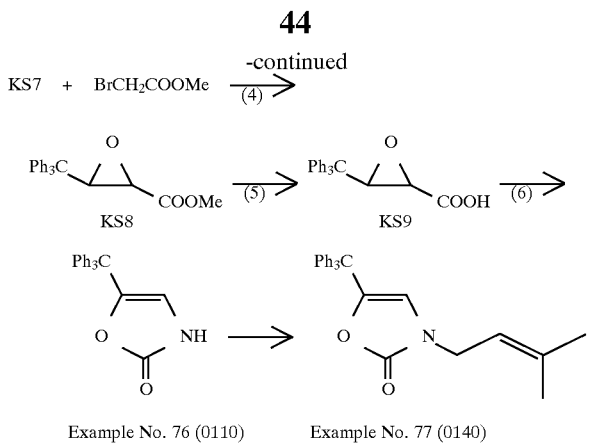

Example No. 76 (0110)    Example No. 77 (0140)

EXAMPLE 76
Compound 0110

(1) Triphenylacetic acid (20.0 g, 69.4 mmol) was suspended in acetone (250 ml), and anhydrous potassium carbonate (57.5 g, 69.4 mmol×6) and dimethylsulfate acid (16.4 ml, 69.4 mmol×2.5) were added, and the mixture was stirred at room temperature for 50 minutes. The reaction mixture was concentrated, and then partitioned between ethyl acetate and 2N hydrochloric acid. The organic layer was washed in turn with water and brine, dried. and concentrated. The crystal precipitated was washed with ether to give 20.6 g of compound KS5 (yield 98%).

Melting point: 185°–186° C.
¹H NMR (CDCl₃): δ 3.80 (s, 3H), 7.10–7.36 (m, 15H)
IR (Nujol): 1730, 1595, 1486, 1218, 1196, 1179, 1006 cm⁻¹
Elemental analysis (%) C₂₁H₁₈O₂ Calcd.:C, 83.42; H, 6.00 Found:C, 83.43; H, 6.09

(2) Lithium aluminum hydride (2.56 g, 67.5 mmol) was suspended in THF (150 ml), to which was added a solution of the compound KS5 (20.4 g, 67.5 mmol) in THF (300 ml) at room temperature over 45 minutes, and the mixture was stirred for additional 30 minutes. Then, ethyl acetate and water were added in turn with ice cooling to decompose the excessive reagent. The reaction solution was concentrated and the residue was partitioned between ethyl acetate and 2N hydrochloric acid. The organic layer was washed in turn with water and brine, and concentrated. The crystal precipitated was washed with ether/hexane to give 18.03 g of the compound KS6 (yield 97%).

Melting point: 108°–109° C.
¹H NMR (CDCl₃): δ 4.65 (s, 2H), 7.13–7.36 (m, 15H)
IR (Nujol): 3590, 1596, 1490, 1052, 1039 cm⁻¹
Elemental analysis (%) C₂₀H₁₈O Calcd.: C, 87.56; H, 6.61 Found: C, 87.40; H, 6.67

(3) To a solution of dimethyl sulfoxide (11.11 ml, 65.2 mmol×2.4) in methylene chloride (100 ml), oxalyl chloride (6.83 ml, 65.2 mmol×1.2) was added at −55° C., and the mixture was stirred at the same temperature for 40 minutes. To the reaction mixture was dropwise added a solution of the compound KS6 (17.90 g, 65.2 mmol) in methylene chloride (200 ml) at −55° C. over 20 minutes. After stirring at the same temperature for 40 minutes, triethylamine (27.28 ml, 65.2 mmol×3) was dropwise added at the same temperature. After stirring at −55° C. for 10 minutes, a cooling bath was removed and the temperature was gradually increased to room temperature. The organic layer was partitioned between ethyl acetate and 2N hydrochloric acid. The reaction solution was washed in turn with water, aqueous 5% NaHCO₃ solution and brine, then dried. After concentration, the crystal precipitated was washed with ether/hexane to give 16.91 g of the compound KS7 (yield 95%).

Melting point: 102°–104° C.

$^1$H NMR (CDCl$_3$): δ 7.00–7.13 (m, 6H), 7.26–7.41 (m, 9H), 10.29 (s, 1H)

IR (Nujol): 1722, 1596, 1580, 1491, 1447, 1088, 754, 700, 587 cm$^{-1}$

Elemental analysis (%) C$_{20}$H$_{16}$O Calcd.: C, 88.20; H, 5.92 Found: C, 88.02; H, 6.12

(4) To a solution of diisopropylamine (11.10 ml, 60.9 mmol×1.3) in THF (60 ml), a n-butyllithium/1.6N hexane solution (49.49 ml) was added at −25 ° C., and the mixture was stirred at the same temperature for 30 minutes. The mixture was dropwise added to a solution of the compound KS7 (16.59 g, 60.9 mmol) and methyl bromoacetate (6.92 ml, 60.9 mmol×1.2) in THF (80 ml) at −25° C. After stirring at −25° C. for 15 minutes, a cooling bath was removed and the temperature was gradually increased to room temperature. After the reaction solution was concentrated, the resulting residue was partitioned between ethyl acetate and 2N hydrochloric acid. The organic layer was washed in turn with water, aqueous 5% NaHCO$_3$ solution and brine, dried, and then concentrated. The resulting residue was purified by silica gel column chromatography and recrystallized with methanol to give 9.69 g of the compound KS8 (yield 46%).

Melting point: 110°–112° C.

$^1$H NMR (CDCl$_3$): δ 3.04 (d, J=2.0 Hz, 1H), 3.79 (s, 3H), 4.25 (d, J=2.0 Hz, 1H), 7.03–7.19 (m, 6H), 7.22– 7.38 (m, 9H)

IR (Nujol): 1744, 1595, 1493, 1343, 1269, 1215, 1083, 1034, 1001, 949, 903, 870, 838 cm$^{-1}$ Elemental analysis (%) C$_{23}$H$_{20}$O$_3$ Calcd.: C, 80.21; H, 5.85 Found: C, 80.13; H, 5.99

(5) The compound KS8 (6.53 g, 19.0 mmol) was dissolved in dimethyl sulfoxide (100 ml) and an aqueous 1N potassium hydroxide solution (37.9 ml, 19.0 mmol×2) was added at 0° C., and the mixture was stirred at 0° C. for 5 minutes. The reaction solution was partitioned between ethyl acetate and diluted hydrochloric acid containing ice. The organic layer was washed in turn with water and brine. After the organic layer was dried and concentrated, the resulting residue was recrystallized from ether/hexane to give 5.27 g of the compound KS9 (yield 84%).

Melting point: 142°–146° C. (decomposition point)

$^1$H NMR (DMSO): δ 2.67 (d, J=2.0 Hz, 1H), 4.30 (d, J=2.0 Hz, 1H), 6.98–7.14 (m, 6H), 7.26–7.42 (m, 9H)

IR (Nujol): 2560, 1724, 1596, 1492, 1270, 1228, 752, 743, 698 cm$^{-1}$

Elemental analysis (%) C$_{22}$H$_{18}$O$_3$ Calcd.: C, 79.98; H, 5.49 Found: C, 79.61 ; H, 5.71

(6) The compound KS9 (7.11 g, 21.5 mmol) was suspended in methylene chloride (100 ml) and oxalyl chloride (6.57 ml, 21.5 mmol×3.5) and two drops of dimethylformamide were added at 0° C., and the mixture was stirred at room temperature for 40 minutes. The reaction solution was concentrated, and THF was added to the residue and was concentrated again to give a pale yellow crystal. To the crystal, THF (100 ml) and trimethylsilylazide (14.28 ml, 21.5 mmol×5.0) were added at room temperature, and the mixture was refluxed at 85° C. for 5 hours and 15 minutes. The reaction solution was cooled, and then concentrated. The residue was partitioned between chloroform/methanol (9:1) and water. The aqueous layer was extracted with chloroform/methanol (9:1) and the organic layers were combined . This organic layer was washed with water and dried, then concentrated to give a crystal which was washed with ether to give 2.19 g of compound 0110 (yield 31%).

Melting point: >250° C.

$^1$H NMR (DMSO): δ 6.32 (s, 1H), 6.98–7.08 (m, 6H), 7.27–7.41 (m, 9H), 10.66 (s, 1H)

IR (Nujol): 3160, 3110, 1768, 1728, 1102, 962 cm$^{-1}$

Elemental analysis (%) C$_{22}$H$_{17}$NO$_2$.0.4H$_2$O Calcd.: C, 78.98 ; H, 5.36 ; N, 4.19 Found: C, 79.09; H, 5.31; N, 4.46

EXAMPLE 77

Compound 0140

The compound KS10 (100 mg, 305 μmol) was dissolved in dimethylformamide (4 ml) and a solution of prenyl bromide (228 mg, 305 μmol×5.0) in dimethylformamide (1 ml) was added at room temperature and sodium hydride (13.4 mg, 305 μmol×1.1) was added at 0° C., and the mixture was stirred at room temperature for 2 hours. The reaction solution was partitioned between ethyl acetate and 2N hydrochloric acid. The organic layer was washed in turn with water and brine, was dried and then concentrated. The crystal precipitated was washed with ether to give 76 mg of compound 0140 (yield 63%).

Melting point: 163°–165° C.

$^1$H NMR (CDCl$_3$): δ 1.68 (s, 3H), 1.73 (s, 3H), 4.12 (d, J=4.7 Hz, 2H), 5.13–5.26 (m, 1H), 6.00 (s, 1H), 7.08–7.17 (m, 6H), 7.24–7.35 (m, 9H)

IR (Nujol): 1757, 1491, 757, 743, 701

Elemental analysis (%) C$_{27}$H$_{25}$NO$_2$.0.1H$_2$O Calcd.: C, 81.62; H, 6.39; N, 3.65 Found:C, 81.56; H, 6.38; N, 3.65

EXAMPLES 78 TO 80

According to the method similar to that described in Example 77, the reaction was conducted to give the compounds listed in the following table.

TABLE 9

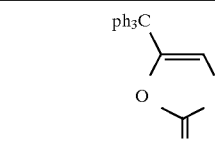

| Example No. | Substituent: R | Melting point (°C.) | IR (cm$^{-1}$) |
|---|---|---|---|
| 78 (0114) | —CH$_2$—⌬ | 150–151 | (Nijol) 3150, 1752, 1475, 1394, 744, 700, 693 |

TABLE 9-continued

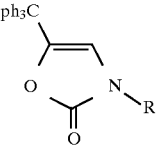

| Example No. | Substituent: R | Melting point (°C.) | IR (cm⁻¹) |
|---|---|---|---|
| 79 (0114) | PMZ | 167–169 | (Nijol) 1830, 1738, 1615, 1517, 1053, 1032 |
| 80 (0120) | —(CH₂)₃—O—⟨phenyl⟩—CF₃ | 194–195 | (Nijol) 3130, 1754, 1740, 1614, 1322, 1260, 1242, 1176, 1159, 1111, 1050 |

EXAMPLE 81

Compound 0029

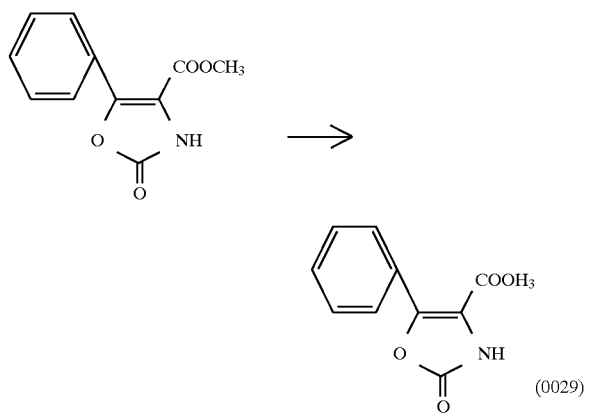

The compound described by Chung-gi et Shin at. al. [Chem. Lett., 1171 (1982)] was used as a starting material. To a solution of the methyl ester (1.50 g) in methanol (15 ml), 1N-NaOH (13.7 ml) was added and the mixture was heated under reflux for 2 hours. The reaction solution was poured into water, acidified with 2N-HCl, and then extracted with methyl ethyl ketone. The extract was washed with water and dried over magnesium sulfate, then concentrated under reduced pressure to give a crystalline residue. The residue was washed with ethyl ether to give 1.183 g of the objective compound (0029) (91.0%).

Melting point: 215°~216° C. (with decomposition)

Elemental analysis; $C_{10}H_7NO_4$ Calcd. C: 58.54 H: 3.44 N: 6.83 Found C: 58.44 H: 3.56 N: 6.78

IR (νmax cm⁻¹, Nujol); 3185 br, 1748, 1760, 1639

NMR d-DMSO δ ppm; 3.37 (br, 1H), 7.40~7.56 (m, 3H), 7.84~7.98 (m, 2H), 11.4 (s, 1H)

EXAMPLE 82

Compound 0030

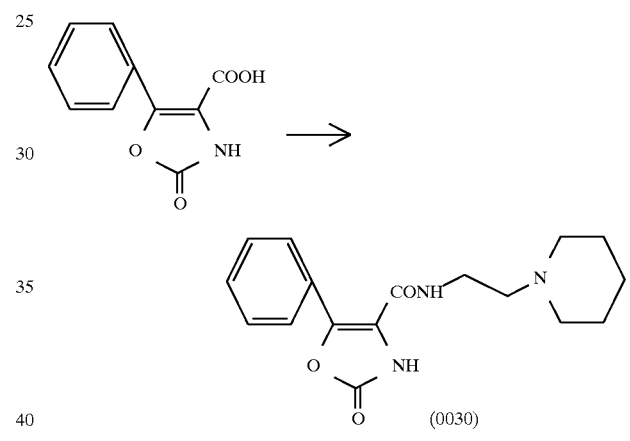

To a solution of the above carboxylic acid (205 mg, 1 mmol) in tetrahydrofuran (10 ml) and dimethylformaide (5 ml), 1-ethyl-3-(3-dimethylaminopropyl)carbodiimide hydrochloride (WSCD.HCl) (192 mg, 1 mmol) and N-hydroxybenzotriazole (135 mg, 1 mmol) were added, and the mixture was stirred for 30 minutes. Then, N-(2-aminoethyl)piperizine (157 μl, 1.1 mmol) was added and the mixture was stirred at room temperature for 4 hours. The reaction solution was poured into water, and extracted with methyl ethyl ketone. The extract was washed with brine and dried over magnesium sulfate, and then concentrated under reduced pressure. The residue was subjected to $SiO_2$ column chromatography and fractions eluted with methylene chloride/methyl alcohol (10:1) was collected to give a foam-like residue (228 mg). The residue was washed with ethyl ether to give 193 mg of the objective compound as an amorphous form (61.0%).

Elemental analysis; $C_{17}H_{21}N_3O_3 \cdot 0.7H_2O$ Calcd. C: 62.25 H: 6.88 N: 12.81 Found C: 62.51 H: 7.02 N: 12.53 5 μg/minutes hygroscopicity IR νNujol max cm⁻¹; 3255, 1769, 1635, 1596, 1510

NMR δ d-MeOH ppm; 1.47~1.79 (m, 6H), 2.72~2.90 (m, 6H), 3.57 (t, J=6 Hz, 2H), 7.34~7.49 (m, 3H), 7.80~7.90 (m, 2H)

EXAMPLE 83

Compound 0034

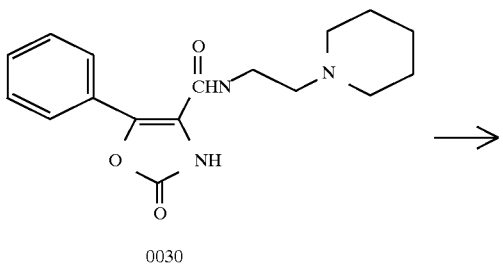

0030

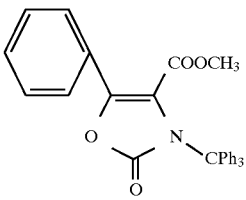

0034

The compound produced in Example 82 was converted into a quaternary salt with $CH_3I$ by a conventional method.

Yield: 61%

Melting point: 200°~201° C.

Elemental analysis; $C_{18}H_{24}N_3O_3I \cdot 0.2H_2O$ Calcd. C: 46.90 H: 5.34 N: 9.12 I: 27.54 Found C: 46.69 H: 5.25 N: 9.20 I: 27.53

IR (Nujol) vmax ($cm^{-1}$): 3280, 3135, 1778, 1667

NMR δ $CD_3OD$ (ppm): 1.60~2.00 (m, 6H), 3.17 (s, 3H), 3.37~3.83 (m, 8H), 7.40~7.50 (m, 3H), 7.74~7.87 (m, 2H)

EXAMPLE 84

Compound 0079

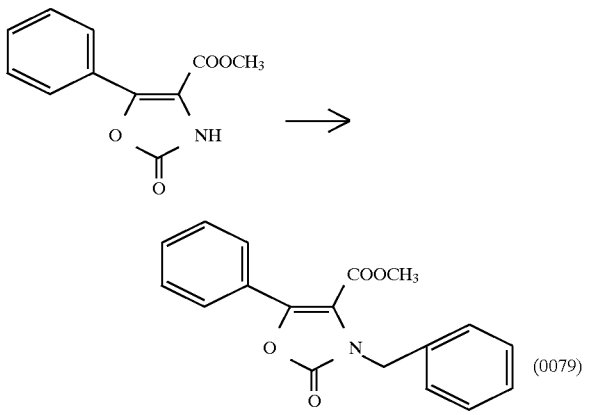

To a suspension of 60% sodium hydride (66 mg, 1.2×1.37 mmol) in dimethylformamide (2 ml), a solution of a methyl ester (300 mg, 1.37 mmol) in dimethylformamide (1.5 ml) was added under argon stream with ice cooling. After stirring at the same temperature for 10 minutes, benzyl bromide (244 μl, 1.5×1.37 mmol) was added, and the mixture was stirred at room temperature for one hour. The reaction solution was poured into water, and extracted with ethyl acetate. The extract was washed in turn with 2N-HCl, 5% $NaHCO_3$ and $H_2O$, then dried over magnesium sulfate and concentrated under reduced pressure. The residue was subjected to $SiO_2$ column chromatography and fractions eluted with n-hexane/ethyl acetate (4:1) were collected, followed by recrystallization from n-hexane to give 270 mg of the objective compound (63.7%).

Melting point: 51°~52° C.

Elemental analysis; $C_{18}H_{15}NO_4$ Calcd. C: 69.89 H: 4.89 N: 4.53 Found C: 69.96 H: 4.82 N: 4.64

IR v$CHCl_3$ max $cm^{-1}$; 1765, 1722, 1498

NMR δ $CDCl_3$ ppm; 3.74 (s, 3H), 5.18 (s, 2H), 7.28~7.48 (m, 8H), 7.68~7.78 (m, 2H)

EXAMPLE 85

Compound 0080

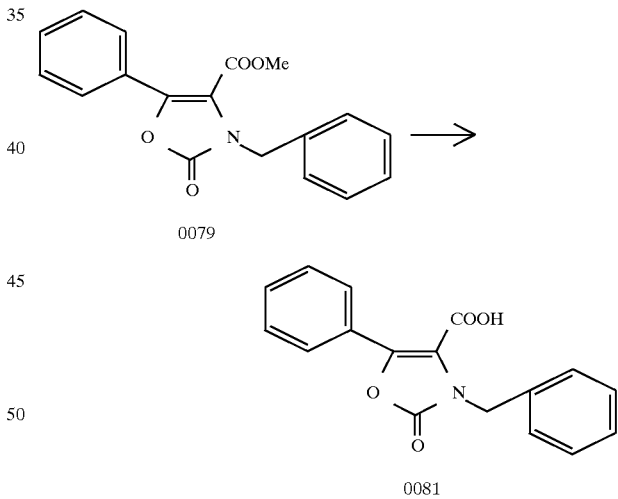

Yield: 75%

Melting point: 160°~163° C.

Elemental analysis; $C_{30}H_{23}N_1O_4$ Calcd. C: 78.07 H: 5.02 N: 3.04 Found C: 78.31 H: 4.94 N: 3.05

IR ($CHCl_3$) vmax ($cm^{-1}$): 1770, 1732, 1600, 1498

NMR δ $CDCl_3$ (ppm): 3.21 (s, 3H), 7.20~7.63 (m, 20H)

EXAMPLE 86

Compound 0081

The compound 0079 produced in Example 84 was hydrolyzed with 1N-NaOH/MeOH by a conventional method to give compound 0081.

Yield: 82%

Melting point: 179°~182° C.

Elemental analysis; $C_{17}H_{13}NO_4$ Calcd. C: 69.14 H: 4.44 N: 4.74 Found C: 68.89 H: 4.42 N: 4.71

IR (Nujol) vmax ($cm^{-1}$): 2220~3290 (br), 1729, 1697, 1617, 1498

NMR ($d_6$-DMSO) δ ppm: 2.80~4.10 (br, 1H), 5.11 (s, 2H), 7.20~7.55 (m, 8H), 7.70~7.80 (m, 2H)

EXAMPLE 87

Compound 0082

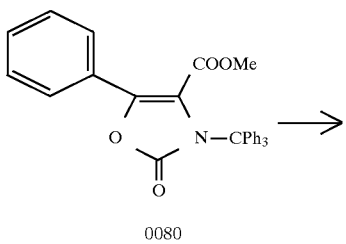

Melting point: 208~210 (decomposition)
NMR (d$_6$-DMSO) δ (ppm): 3.38 (br, 1H), 7.40~7.52 (m, 12H), 7.84~7.95 (m, 8H)
IR (Nujol) νmax (cm$^{-1}$): 2500~3350 br, 1745, 1694, 1640, 1480, 1375

EXAMPLES 88 TO 89

Synthesis of

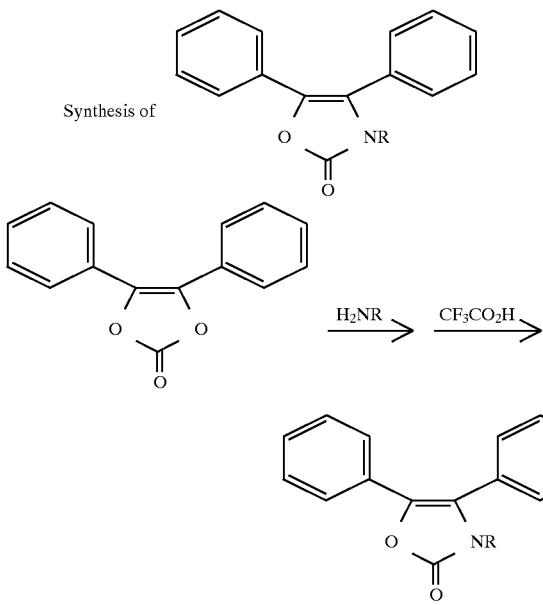

The amine (1 eq) was added to a solution of 4,5-diphenyl-1,3-dioxol-2-one in DMF (4 ml), and the mixture was stirred at room temperature. After the completion of the reaction, ethyl acetate (8 ml) and 0.5N hydrochloric acid (10 ml) were added, and the mixture was stirred and extracted. The organic layer was washed with water, and then dried over Na$_2$SO$_4$. After the solvent was distilled off under reduced pressure, CF$_3$CO$_2$H was added to the residue at room temperature, and the solution was stirred overnight. After CF$_3$CO$_2$H was distilled off under reduced pressure, CH$_2$Cl$_2$ was added and the mixture was washed with alkali and water, then dried over Na$_2$SO$_4$. After the organic solvent was distilled off, the residue was recrystallized from EtOH.

Physico-chemical properties of the resulting compounds are shown in Examples 88 and 89.

EXAMPLE 88

Compound 0092

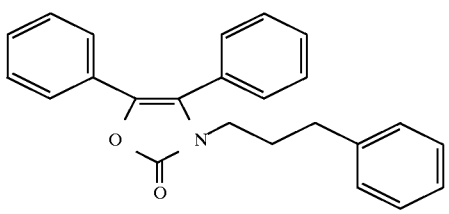

White crystal
Melting point: 99°~101° C.
$^1$H-NMR (CDCl$_3$) δ: 1.74–1.90 (2H, m), 2.52 (2H, t, J=7.5 Hz), 3.52 (2H, t, J=7.5 Hz), 6.97–7.52 (15H, m)
(M,S)m/z 355 (M$^+$)
Elemental analysis Calcd.: C: 81.1 H: 5.96 N: 3.94 Found: C: 80.94 H: 5.95 N: 3.93
IR (cm$^{-1}$, KBr): 695, 745, 760, 1365, 1445, 1495, 1600, 1755, 2950, 3020, 3400

EXAMPLE 89

Compound 0108

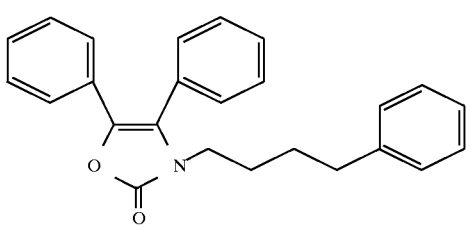

Colorless oily product
$^1$H-NMR (CDCl$_3$) δ: 1,41–1.56 (4H, m), 2.51 (2H, t, J=7.5 Hz), 3.50 (2H, t, J=7.5 Hz), 7.05–7.53 (15H, m)
M,S m/z: 370[M+H]$^+$ 739[2M+H]$^+$
IR (cm$^{-1}$, neat): 700, 755, 765, 1025, 1055, 1360, 1390, 1450, 1500, 1605, 1760, 2950

Reference Example 2

Synthesis of

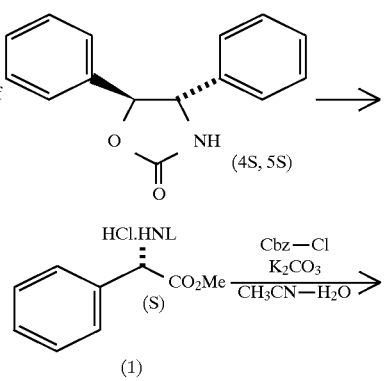

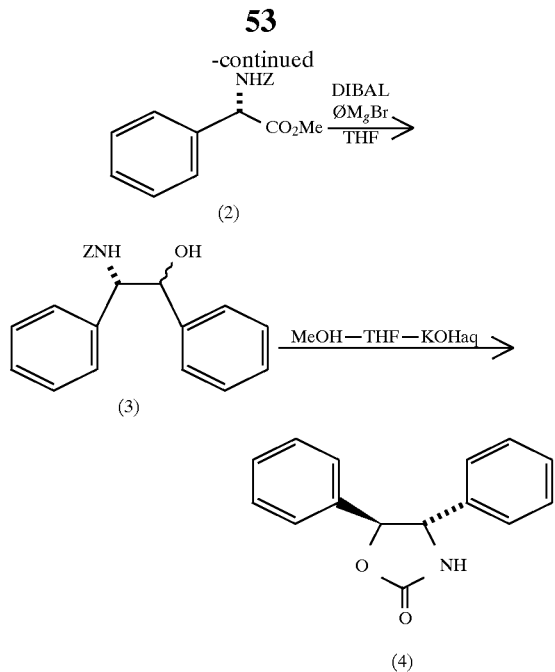

(2)

(3)

(4)

Process 1: (1)→(2)

To a solution of L-(+)-phenylglycine methyl ester hydrochloride (1 g) and CbzCl (1.1 eq, 0.928 g) in $CH_3CN$/Water (2:1), an aqueous solution (50 ml) of $K_2CO_3$ (5 eq) was dropwise added at 0° C. After completion of the reaction, the reaction solution was extracted with ethyl acetate and purified with silica gel to give 1.42 g of a white solid (yield 96%).

Data (S isomer) of compound (2)

$^1$H-NMR (CDCl$_3$) δ: 3.72 (s, 3H), 5.09 (s, 2H), 5.38 (d, 1H, J=7.5 Hz), 5.82~5.86 (br, 1H) 7.34 (s, 10H)

$[α]_D$=−114.6°±1.5° (CHCl$_3$, C=1.002, 24° C.)

Melting point: 66° C.

Process 2: (2)→(4)

Et$_2$O (100 ml) in which the compound (2) (1.89 g) was dissolved was cooled to −78° C. under N$_2$ atmosphere and DIBAL (THF solution) (1.2 eq) was dropwise added at the same temperature. After one hour, a solution of phenyl magnesium bromide (4 eq) in THF was dropwise added, and the mixture was heated to room temperature. After stirring overnight, the reaction was terminated with aqueous NH$_4$Cl. Then, the reaction solution was extracted with ethyl acetate and purified by silica gel to give 1.46 g of a white solid (compound (3), yield 67%).

The compound (3) was dissolved in a mixed solvent [7.5N KOH:THF:MeOH=4:2:1), and the mixture was stirred at room temperature overnight. After neutralizing with 1N hydrochloric acid, the mixture was extracted with ethyl acetate and purified by silica gel chromatography.

Data (S isomer) of compound (4) (4s, 5s)

$^1$H-NMR (CDCl$_3$) δ: 4.76 (d, 1H, J=7.4 Hz), 5.30 (d, 1H, J=74 Hz), 5.90 (s, 1H), 7.26–7.41 (m, 10H)

$[α]_D$=−63.7°±1.0° (C=1.008, CHCl$_3$, 24° C.)

Melting point: 131° C.

Reference Example 3

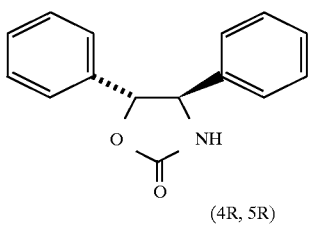

(4R, 5R)

According to the method similar to that described in Reference Example 2 except for using D-(−)-phenylglycine methyl ester hydrochloride as a starting material, the reaction was conducted.

$^1$H-NMR (CDCl$_3$) δ: 4.77 (d, 1H, J=7.4 Hz), 5.26 (d, 1H, J=7.4 Hz), 6.45 (s, 1H), 7.27~7.42 (m, 10H)

$[α]_D$=+62.4°±1.0° (C=1.013, CHCl$_3$, 25° C.)

Melting point: 133° C.

M.S: m/z 239 (M$^+$), 107 (base peak)

EXAMPLE 90

Compound 0161

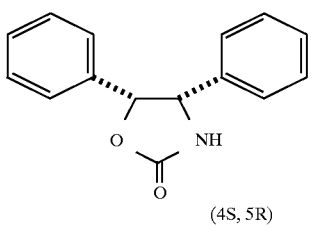

(4S, 5R)

(1R, 2S)-(−)-2-Amino-1,2-diphenylethanol (8.58 g) and Et$_3$N (1 ml) were dissolved in THF (150 ml). After the solution was cooled to 0° C., triphosgene 3.86 g) was added and the mixture was heated to room temperature after stirring for 5 minutes. After completion of the reaction, the reaction was terminated with water. After stirring for 30 minutes, the reaction solution was extracted with ethyl acetate. After the organic solvent was distilled off, the residue was recrystallized from ethyl acetate to give 6.44 g of compound 0161 as a white solid (yield 67%).

$^1$H-NMR (CDCl$_3$) δ: 5.19 (d, 1H, J=8.2 Hz), 5.96 (d, 1H, J=8.2 Hz), 5.76 (s, 1H), 6.92–7.14 (m, 10H)

$[α]_D$=−75.4°±1.1° (C=1.016, CHCl$_3$, 23° C.)

Melting point: 232° C.

EXAMPLE 91

Compound 0180

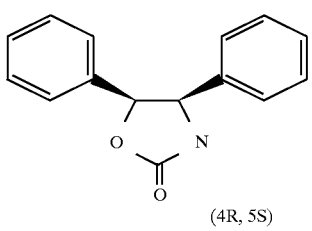

(4R, 5S)

According to the method similar to that described in Example 90 except for using (1S, 2R)-(+)-2-amino-1,2-diphenylethanol as a starting material, the reaction was conducted.

$^1$H-NMR (CDCl$_3$) δ: 5.19 (d, 1H, J=8.2 Hz), 5.96 (d, 1H, J=8.2 Hz), 5.46 (s, 1H), 6.92–7.15 (m, 10H)

[α]$_D$=+75.3°±1.2° (C=1.001, CHCl$_3$, 23.5° C.)
Melting point: 229° C.
M.S: m/z 240[M+H]$^+$, 479[2M+H]$^+$
IR: cm$^{-1}$ KBr 3400, 3270, 1745, 1710, 1496, 1452, 1351, 1235, 1092, 979, 762, 715, 696

Reference Example 4

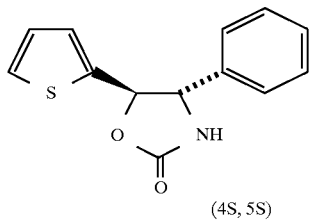

(4S, 5S)

According to the method similar to the production process of (4S, 5S)-4,5-diphenyl-oxazolin-2-one in Reference Example 2 except for using thiophenyl magnesium bromide in place of phenyl magnesium bromide, the reaction was conducted.

$^1$H-NMR (CDCl$_3$) δ: 4.95 (d, 1H, J=7.5 Hz), 5.50 (d, 1H, J=7.5 Hz), 5.59 (br, 1H) 6.75–7.10 (m, 2H), 7.28–7.48 (m, 6H)
[α]$_D$=−133.2°±1.7° (C=1.000, CHCl$_3$, 24° C.)
Melting point: 138° C.

Reference Example 5

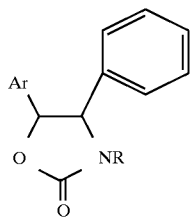

To a DMF solution of oxazoline was added alkyl halide (more than 1.5 eq), then NaH (2 eq) at 0° C. under N$_2$ atmosphere. After completion of the reaction, the reaction solution was extracted with ethyl acetate and purified by silica gel chromatography.

Example 92

Compound 0212

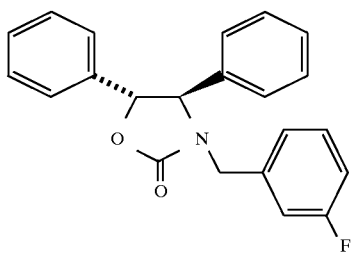

To a solution of (4R, 5R)-4,5-diphenyl-oxazolin-2-one (84.5 mg, 0.353 mmol) in DMF was added 2-fluoro-benzyl chloride (1,7 eq), then NaH (3 eq) at 0° C. under N$_2$ atmosphere, and the mixture was stirred while maintaining the temperature at 0° C. After completion of the reaction, the reaction solution was extracted with ethyl acetate and purified by silica gel chromatography to give a colorless oily product (107.1 mg, yield 87%).

Colorless oily product
$^1$H-NMR (CDCl$_3$) δ: 3.74 (1H, d, J=15 Hz), 4.31 (1H, d, J=7.5 Hz), 4.89 (1H, d, J=15 Hz), 5.30 (1H, d, J=7.5 Hz), 6.78–7.48 (14H, m)
M,S: 347 (M$^+$) 132 (base peak)

EXAMPLES 93 TO 109

According to the method similar to that described above, the following compounds were synthesized.

EXAMPLE 93

Compound 0168

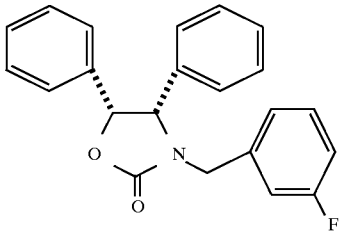

White crystal
Melting point: 109°~110° C.
$^1$H-NMR (CDCl$_3$) δ: 3.71 (1H, d, J=15 Hz), 4.82 (1H, d, J=7.5 Hz), 5.01 (1H, d, J=15 Hz), 5.81 (1H, d, J−7.5 Hz), 6.79–7.34 (14H, m)
M,S m/z 347 (M$^+$) 132 (base peak)
[α]$_D$ +79.8°±1.2° (C=1.00, CHCl$_3$, 23° C.)

EXAMPLE 94

Compound 0169

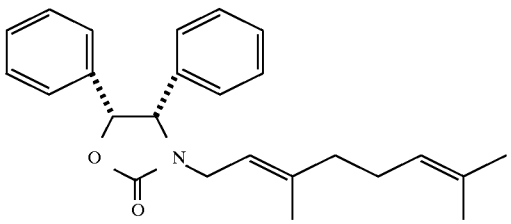

White crystal
Melting point: 78°~79° C.
$^1$H-NMR (CDCl$_3$) δ: 1.28 (3H, s), 1.63 (3H, s), 1.73 (3H, s), 1.94–2.12 (4H, m), 3.40 (1H, dd, J=10 Hz, 15 Hz), 4.25 (1H, dd, J=6.3 Hz, 15 Hz), 4.99 (1H, d, J=8.8 Hz), 5.04–5.24 (2H, m), 5.81 (1H, d, J=8.8 Hz), 6.78–7.20 (10H, m)
[α]$_D$ +25.3°±0.7° (C=1.00, CHCl$_3$, 23° C.)

EXAMPLE 95

Compound 0181

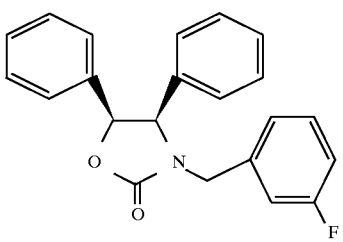

White crystal
Melting point: 106°~107° C.

¹H-NMR (CDCl₃) δ: 3.71 (1H, d, J=15 Hz), 4.83 (1H, d, J=8.8 Hz), 5.00 (1H, d, J=15 Hz), 5.80 (1H, d, J=8.8 Hz), 6.78–7.35 (14H, m)

M,S m/z 348[M+H]⁺ 695 [2M+H]⁺

Elemental analysis Calcd.: C: 76.07 H: 5.22 F: 5.47 N: 4.03 Found: C: 76.00 H: 5.32 F: 5.55 N: 4.03

[α]$_D$ −82.4°±1.2° (C=1.00, CHCl₃, 24° C.)

IR (cm⁻¹, KBr) 698, 705, 764, 1018, 1227, 1417, 1455, 1745, 3430 (br)

EXAMPLE 96

Compound 0182

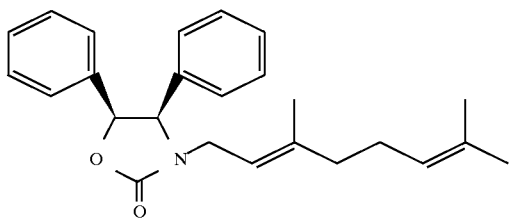

White crystal

Melting point: 80°~81° C.

¹H-NHR (CDCl₃) δ: 1.27 (3H, s), 1.62 (3H, s), 1.72 (3H, s), 1.94–2.12 (4H, m), 3.40 (1H, dd, J=10 Hz, 15 Hz), 4.25 (1H, dd, J=6.3 Hz, 15 Hz), 5.00 (1H, d, J=8.8 Hz), 5.04–5.24 (2H, m), 5.81 (1H, d, J=8.8 Hz), 6.78–7.20 (10H, m)

M,S 376[M+H]⁺, 751[2M+H]⁺

Elemental analysis Calcd.: C: 79.96 H: 7.78 N: 3.73 Found: C: 79.46 H: 7.87 N: 3.79

[α]$_D$ −26.9°±0.7° (C=1.01, CHCl₃, 24° C.)

IR (cm⁻¹, KBr) 698, 760, 1021, 1235, 1425, 1455, 1730, 2910, 3420 (br)

EXAMPLE 97

Compound 0199

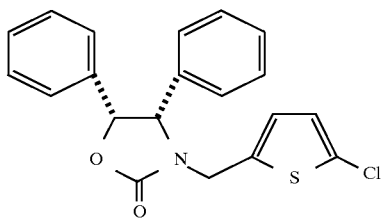

White crystal

Melting point: 96°~97° C.

¹H-NMR (CDCl₃) δ: 3.86 (1H, d, J=15 Hz), 4.96 (1H, d, J=8.8 Hz), 5.01 (1H, d, J=15 Hz), 5.79 (1H, d, J=8.8 Hz), 6.57 (1H, d, J=3.8 Hz), 6.76–7.26 (11H, m)

M,S 369 (M⁺) 180 (base peak)

[α]$_D$ 132.3°±1.7° (C=1.01, CHCl₃, 25° C.)

IR (cm⁻¹, KBr) 695, 760, 802, 995, 1020, 1231, 1369, 1410, 1462, 1497, 1735, 3030, 3440 (br)

EXAMPLE 98

Compound 0213

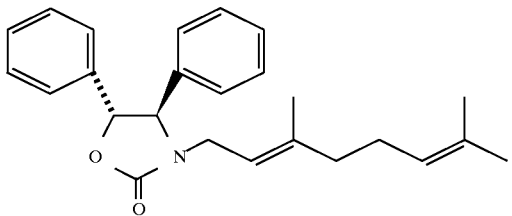

Colorless oily product

¹H-NMR (CDCl₃) δ: 1.26 (3H, s), 1.56 (3H, s), 1.58 (3H, s), 1.84–2.06 (4H, m), 3.40 (1H, dd, J=10 Hz, 13.8 Hz), 4.17 (1H, dd, J=6.3 Hz, 13.8 Hz), 4.48 (1H, d, J=7.5 Hz), 4.95–5.13 (2H, m), 5.22 (1H, d, J=7.5 Hz), 7.18–7.47 (10H, m)

M,S 375 (M⁺) 180 (base peak)

EXAMPLE 99

Compound 0246

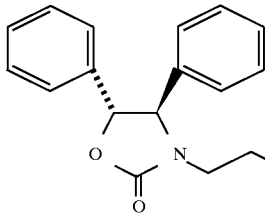

Colorless oily product

¹H-NMR (CDCl₃) δ: 3.86 (1H, d, J=15 Hz), 4.43 (1H, d, J=7.5 Hz), 4.92 (1H, d, J=15 Hz), 5.27 (1H, d, J=7.5 Hz), 6.54 (1H, d, J=3.8 Hz), 6.72 (1H, d, J=3.8 Hz), 7.12–7.51 (10H, m)

M,S m/z 369 (MH⁺) 180 (base peak)

EXAMPLE 100

Compound 0247

White crystal

Melting point: 87°~88° C.

¹H-NMR (CDCl₃) δ: 1.33–1.65 (4H, m), 2.40–2.70 (2H, m), 2.83 (1H, dt, Jd=13.8 Hz, Jt=6.3), 3.54 (1H, dt Jd=13.8 Hz Jt=7.5 Hz), 4.43 (1H, d, J=7.5 Hz), 5.22 (1H, d,=7.5 Hz), 7.00–7.50 (15H, m)

M,S m/z 371 (M⁺) 91 (base peak)

EXAMPLE 101
Compound 0288

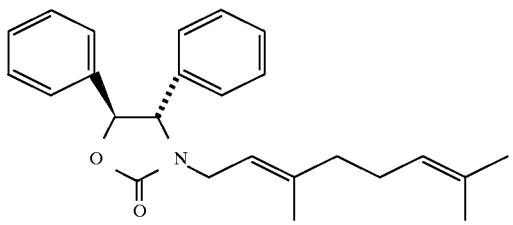

Colorless oily product
$^1$H-NMR (CDCl$_3$) δ: 1.26 (3H, s), 1.55 (3H, s), 1.58 (3H, s), 1.84–2.06 (4H, m), 3.40 (1H, dd, J=10 Hz, 13.8 Hz), 4.17 (1H, d, d, J=6.3 Hz, 13.8 Hz), 4.48 (1H, d, J=17.5 Hz), 4.95–5.13 (2H, m), 5.22 (1H, d, J=7.5 Hz), 7.18–7.47 (10H, m)
M,S m/z 375 (M$^+$) 180 (base peak)
[α]$_D$ −71.3°±1.2° (C=0.96, CHCl$_3$, 23° C.)
Elemental analysis Calcd.: C: 79.96 H: 7.78 N: 3.73 Found C: 79.68 H: 7.92 N: 3.87
IR (cm$^{-1}$, neat) 700, 760, 1034, 1198, 1278, 1404, 1457, 1760, 2917, 2966

EXAMPLE 102
Compound 0289

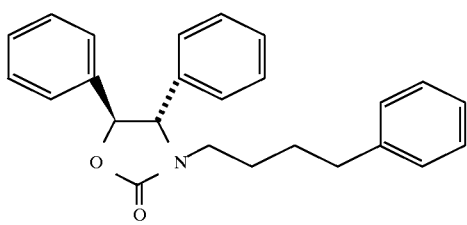

Colorless oily product
$^1$H-NMR (CDCl$_3$) δ: 1.33–1.64 (4H, m), 2.40–2.70 (2H, m), 2.83 (1H, dt, Jd=13.8 Hz, Jt=6.3 Hz), 3.54 (1H, dt, Jd=13.8 Hz Jt=7.5 Hz), 4.43 (1H, d, J=7.5 Hz), 5.22 (1H, d, J=7.5 Hz), 7.00–7.48 (15H, m)
M,S m/z 371 (M$^+$) 91 (base peak)

EXAMPLE 103
Compound 0296

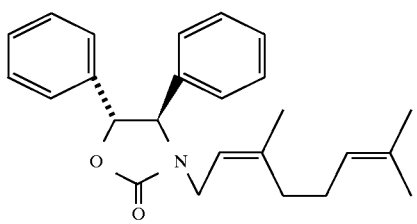

Colorless oily product
$^1$H-NMR (CDCl$_3$) δ: 1.47 (3H, s), 1.56–1.92 (10 H, m), 3.40 (1H, dd, J=8.8 Hz, 15 Hz), 4.06–4.18 (1H, m), 4.51 (1H, d, J=7.5 Hz), 4.82–4.94 (1H, m), 5.04–5.14 (1H, m), 5.21 (1H, d, J=7.5 Hz), 7.20–7.50 (10H, m)
M,S m/z 375 (M$^+$) 180 (base peak)
[α]$_D$ +91.7°±1.3° (C=1.03, CHCl$_3$, 26° C.)
Elemental analysis Calcd.: C: 79.96 H: 7.78 N: 3.73 Found: C: 79.61 H: 7.87 N: 3.85

EXAMPLE 104
Compound 0313

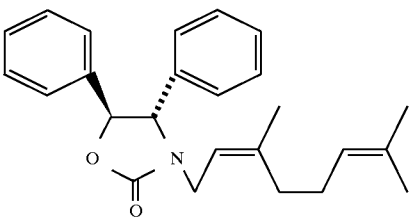

Colorless oily product
$^1$H-NMR (CDCl$_3$) δ: 1.47 (3H, s), 1.56–1.92 (10H, m), 3.39 (1H, dd, J=8.8 Hz, J=15 Hz), 4.06–4.18 (1H, m), 4.51 (1H, d, J=7.5 Hz), 4.82–4.94 (1H, m), 5.04–5.14 (1H, m), 5.21 (1H, d, J=7.5 Hz), 7.20–7.50 (10H, m)
M,S m/z 375 (M$^+$) 180 (base peak)

EXAMPLE 105
Compound 0315

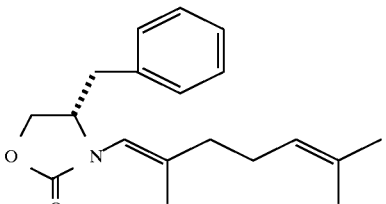

Colorless oily product
$^1$H-NMR (CDCl$_3$) δ: 1.61 (3H, s), 1.66 (3H, s), 1.71 (3H, s), 2.00–2.20 (4H, m), 2.63 (1H, dd, J=7.5 Hz, 13.8 Hz), 3.12 (1H, dd, J=3.8 Hz, 11.3 Hz), 3.75 (1H, dd, J=7.5 Hz, 13.8 Hz), 3.88–4.24 (4H, m), 5.00–5.24 (2H, m), 7.07–7.40 (5H, m)
M,S m/z 313 (M$^+$) 69 (base peak)
Elemental analysis Calcd.: C: 76.64 H: 8.68 N: 4.47 Found: C: 75.78 H: 8.67 N: 4.39
[α]$_D$ −92.4°±1.2° (C=1.28, CHCl$_3$, 25° C.)

EXAMPLE 106
Compound 0325

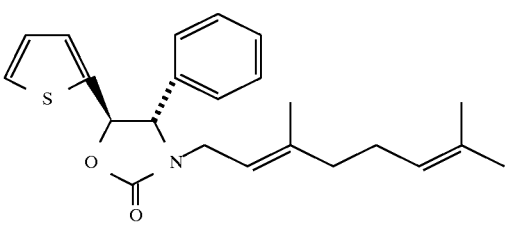

Colorless oily product
$^1$H-NMR (CDCl$_3$) δ: 1.29 (3H, s), 1.56 (3H, s), 1.64 (3H, s), 1.90–2.05 (4H, m), 3.42 (1H, dd, J=15 Hz, 8.8 Hz), 4.12–4.23 (1H, m), 4.66 (1H, d, J=7.6 Hz), 5.41 (1H, d, J=7.6 Hz), 6.95–7.02 (2H, m), 7.21–7.46 (6H, m)
M,S 381 (M$^+$) 186 (base peak)
Elemental analysis Calcd.: C: 72.41 H: 7.13 N: 3.67 S: 8.4 Found: C: 72.37 H: 7.25 N: 3.72 S: 8.31
[α]$_D$ −123.5°±2.0° (C=0.80, CHCl$_3$, 23° C.)
IR (cm$^{-1}$, neat) 702, 1378, 1404, 1438, 1454, 1668, 1761, 1916, 2966

EXAMPLE 107

Compound 0346

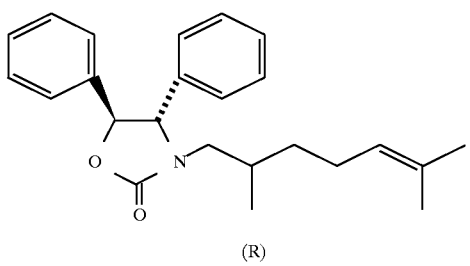

(R)

Colorless oily product

¹H-NMR (CDCl₃) δ: 0.83 (3H, d, J=6.3 Hz), 0.90–1.53 (8H, m), 1.65 (3H, s), 1.78–1.95 (2H, m), 2.70–2.90 (1H, m), 3.45–3.65 (1H, m), 4.53 (1H, d, J=6.3 Hz), 4.94–5.07 (1H, m), 5.23 (1H, d, J=6.3 Hz), 7.20–7.48 (10H, m)

M,S m/z 377 (M+) 180 (base peak)

Elemental analysis Calcd.: C: 79.54 H: 8.28 N: 3.71 Found: C: 79.18 H: 8.34 N: 3.74

$[\alpha]_D$ −28.6±0.7 (C=1.06, CHCl₃, 23° C.)

IR (cm⁻¹, neat) 700, 758, 1022, 1036, 1411, 1457, 1760, 2915, 2962

EXAMPLE 108

Compound 0347

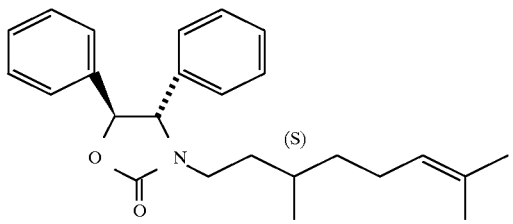

(S)

Colorless oily product

¹H-NMR (CDCl₃) δ: 0.81 (3H, d, J=6.3 Hz), 0.90–1.53 (8H, m), 1.65 (3H, s) 1.78–1.95 (2H, m), 2.70–2.90 (1H, m), 3.45–3.65 (1H, m), 4.52 (1H, d, J=6.3 Hz), 4.94–5.07 (1H, m), 5.23 (1H, d, J=6.3 Hz), 7.20–7.48 (10H, m)

M,S m/z 377 (M⁺) 180 (base peak)

Elemental analysis Calcd.: C: 79.54 H: 8.28 N: 3.71 Found: C: 79.15 H: 8.34 N: 3.76

$[\alpha]_D$ −14.4°±0.5° (C=1.07, CHCl₃, 23° C.)

IR (cm⁻¹, neat) 700, 758, 1022, 1376, 1412, 1457, 1759, 2915, 2962

EXAMPLE 109

Compound 0303

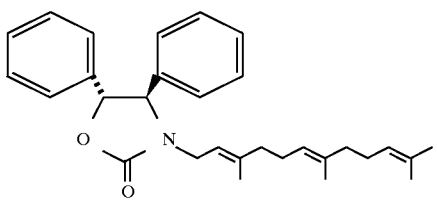

303

¹H-NMR (CDCl₃) δ: 1.27 (s, 3H), 1.56 (s, 3H), 1.59 (s, 3H), 1.68 (s, 3H), 1.80–2.10 (m, 8H), 3.41 (dd, 1H, J=15 Hz, J=10 Hz), 4.16 (dd, 1H, J=15 Hz, J=7.5 Hz), 4.49 (d, 1H, J=8.8 Hz), 4.96–5.16 (m, 3H), 5.21 (d, 1H, J=8.8 Hz), 7.20–7.50 (m, 10H)

M.S m/z 180 (base peak), 443 [M⁺], 444[MH⁺]

EXAMPLES 110 TO 115

According to the method similar to that described above, the following compounds were produced.

TABLE 10

| Example No. | Substituent: R | Melting point (°C.) | IR (cm⁻¹) |
|---|---|---|---|
| 110 (0198) | —(CH₂)₃—⌬ | 118 | (Nijol) 3420, 3030, 2920, 1725, 1496, 1452, 1425, 1275, 1021, 757, 595 |
| 111 (0236) | —CH₂CH₂—N⟨O⟩ | 144–145 | (KBr) 3456, 2959, 2851, 1740, 1455, 1419, 12636, 1118, 702 |

TABLE 10-continued
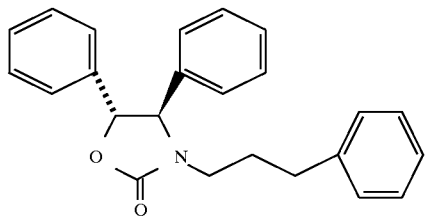
| Example No. | Substituent: R | Melting point (°C.) | IR (cm$^{-1}$) |
|---|---|---|---|
| 112 (0237) | —CH$_2$—(2-quinolinyl) | 135–136 | 3452, 3027, 2912, 1761, 1453, 1389, 1039, 1026, 702 |
| 113 (0244) | —CH$_2$CH$_2$COOCH(Ph)$_2$ | Amorphous | 3449, 3031, 1756, 1455, 1225, 1164, 1025, 760, 697 |
EXAMPLE 114
Compound 0245
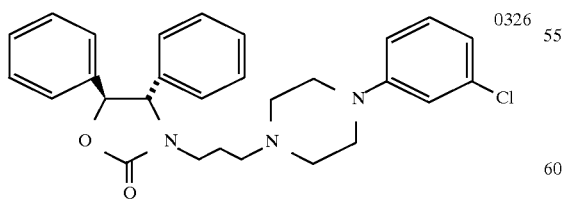
White crystal
Melting point: 83°~84° C.
IR: (KBr) 701, 988, 1154, 1407, 1733, 1744, 2988, 3085, 3451 cm$^{-1}$
M.S m/z 359[M+] 91 (base peak)
$[\alpha]_D$ 16.2°±0.6° (C=1.018, CHCl$_3$, 25° C.)
EXAMPLE 115
Compound 0326
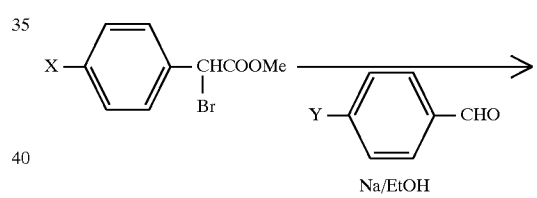
White amorphous powder
IR: (KBr) 700, 763, 987, 1235, 1410, 1456, 1487, 1563, 1594, 1757, 2821, 2942 cm$^{-1}$.
MS m/z 475 [M$^+$] 209 (base peak)
EXAMPLES 116 TO 120
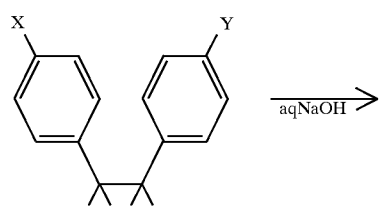
I-31 X = Ph  Y = H
I-39 X = H   Y = Ph
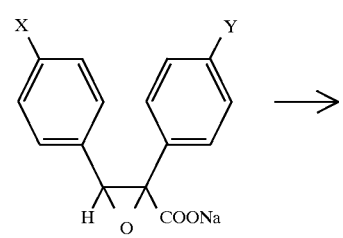
I-32 X = Ph  Y = H
I-40 X = H   Y = Ph

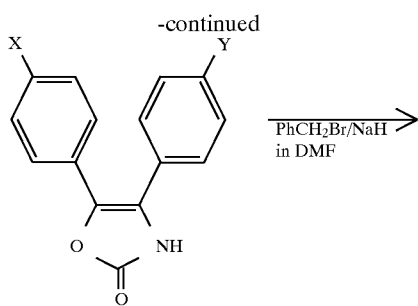

I-42 (0144) X = Y   Y = Ph Example 118
I-34 (0088) X = Ph  Y = H  Example 116

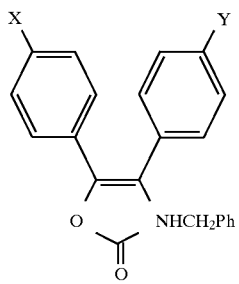

I-42 (0145) X = Y   Y = Ph Example 119
I-35 (0089) X = Ph  Y = H  Example 117

EXAMPLE 116

5-(4-Biphenyl)-4-phenyloxazolin-2-one (I-34) (0088)

(1) Methyl 3-(4-biphenyl)-2,3-epoxy-2-phenyl propionate (I-31)

To a solution of biphenylaldehyde (5.60 g, 30.72 mmol) in MeOH (169 ml), Na (742 mg, 32.26 mmol) and bromomethyl ester (I-30) (7.04 g, 30.72 mmol) were added, and the mixture was stirred at room temperature for 1.5 hours. Water (200 ml) was added to the reaction solution and the crystal precipitated was filtered. The crystal was dissolved in $CH_2Cl_2$ and the solution was dried over $MgSO_4$, and the solvent was distilled off under reduced pressure to give 8.20 g of a crystalline residue. The residue was purified by silica gel chromatography ($SiO_2$ 430 g; eluted with toluene/n-hexane (1:1) and toluene) to give a crystal (3.80 g), which was recrystallized from $CH_2Cl_2$/diethyl ether/n-hexane to give 3.41 g of a colorless needle crystal (33.5%).

Melting point: 148.0°~149.0° C.

Elemental analysis ($C_{22}H_{18}O_3$ (MW=330.383)): Calcd.: C, 79.98; H, 5.49 Found: C, 80.09; H, 5.44

IR ($CHCl_3$): 1738, 1601, 1566, 1488, 1449, 1436, 1412, 1386 cm$^{-1}$

NMR ($CDCl_3$): δ 3.815 (s, 3H), 4.604 (s, 1H), 7.01~7.13 (m, 2H), 7.18~7.43 (m, 10H), 7.43~7.54 (m, 2H)

(2) Sodium 3-(4-biphenyl)-2,3-epoxy-2-phenyl propionate (I-32)

To a solution of an aqueous 1N-NaOH solution (11.9 ml, 11.96 mmol) in methanol (53 ml)/THF (35 ml), methyl ester (I-31) (3.76 g, 11.39 mmol) was dissolved, and the mixture was stirred with ice cooling for 40 minutes, then stirred at room temperature for 3 hours. The solvent of the reaction mixture was distilled off under reduced pressure and the residue was washed with $Et_2O$ to give 3.183 g of a colorless needle crystal (82.6%).

Elemental analysis ($C_{21}H_{15}O_3Na$ (MW=338.338)): Calcd.: C, 74.55; H, 4.47; Na, 6.79 Found: C, 74.50; H, 4.58; Na, 6.81

IR (nujol): 3620, 3405, 3062, 3035, 1610, 1489, 1449, 1392 cm$^{-1}$

NMR ($CD_3OD$): δ 4.415 (s, 1H), 7.03~7.43 (m, 12H), 7.43~7.54 (m, 2H)

The solvent of the washing solution was distilled off under reduced pressure and the residue was acidified by adding aqueous HCl, then the mixture was extracted with ethyl acetate. The ethyl acetate layer was dried, and then the solvent was distilled off to give 686 mg of free carboxylic acid as a colorless crystal (19%).

(3) 5-(4-Biphenyl)-4-phenyloxazolin-2-one (I-34) (0088)

To a solution of a Na salt (I-32) (2.74 g, 8.11 mmol) in THF (40 ml), oxalyl chloride (14.5 ml, 162 mmol) was dropwise added with ice cooling, and the mixture was stirred at the same temperature for one hour and 20 minutes. After stirring at room temperature for additional 1.5 hours, the solvent was distilled off under reduced pressure. The resulting residue was dissolved in THF (40 ml), and then $Me_3SiN_3$ (5.66 ml, 40.55 mmol) was added, and the mixture was heated under reflux for 3 hours and 15 minutes. The solvent of the reaction solution was distilled off and the residue was dissolved in $CHCl_3$/MeOH (9:1), and then the solution was washed with water and dried, then the solvent was distilled off. The resulting crystalline residue of cream color was purified by silica gel chromatography ($SiO_2$: 18.7 g, eluent: $CH_2Cl_2$ & $CH_2Cl_2$/MeOH (19:1)) and recrystallized from THF/diethyl ether/n-hexane to give 244 mg of a colorless needle crystal.

Melting point: 204.0°~207.0° C.

Elemental analysis ($C_{21}H_{15}NO_2$ (MW=313.356)): Calcd.: C, 80.49; H, 4.83 N, 4.47 Found: C, 80.64; H, 4.80; N, 4.51

IR ($CHCl_3$): 3445, 3185, 1763 (sh), 1747, 1668, 1600, 1519, 1486, 1449, 1407 cm$^{-1}$

NMR ($CDCl_3$): δ 7.29~7.50 (m, 6H), 7.50~7.65 (m, 8H), 10.190 (brs, 1H)

EXAMPLE 117

5-(4-Biphenyl)-3-benzyl-4-phenyloxazolin-2-one (I-35) (0089)

To a solution of oxazoline (compound 0088) (1.071 g, 3.30 mmol) produced in Example 116 in DMF (10 ml), NaH (60%, 145 mg, 3.63 mmol) and benzyl bromide (1.18 ml, 9.91 mmol) were added, and the mixture was stirred for 2.5 hours with ice cooling. The reaction solution was poured into ice water and the solution was extracted with ethyl acetate. The ethyl acetate layer was washed with water and dried, and then the solvent was distilled off under reduced pressure to give 2.264 g of a yellow oily product, which was purified by silica gel chromatography ($SiO_2$ 124 g; eluted with toluene~toluene/acetone (19:1)) and recrystallized from EtOH to give 912 mg of a colorless needle crystal (68.4%).

Melting point: 111.5°~112.5° C.

Elemental analysis ($C_{28}H_{21}NO_2$ (MW=403.481)): Calcd.:C, 83.35; H, 5.25; N, 3.47 Found: C, 83.33; H, 5.13; N, 3.50

IR ($CHCl_3$): 1749, 1601, 1520, 1497, 1489, 1457, 1448, 1435, 1410, 1386 cm$^{-1}$

NMR ($CDCl_3$): δ 4.682 (s, 2H), 6.94~7.08 (m, 2H), 7.16~7.62 (m, 17H)

EXAMPLE 118

4-(4-Biphenyl)-5-phenyl-oxazolin-2-one (I-42) (0144)

(1) Methyl 2-(4-biphenyl)-2,3-epoxy-3-phenyl propionate (I-39)

To a solution of bromo acetate (I-38) (3.47 g, 11.37 mmol) in MeOH (62 ml), Na (282 mg, 12.28 mmol) and benzaldehyde (1.16 ml, 11.37 mmol) were added, and the mixture was stirred at room temperature for 4 hours. The solution of benzaldehyde (0.58 ml, 5.69 mmol) and Na (136 mg, 5.91 mmol) in MeOH (7 ml) was further added, and the mixture was stirred at room temperature overnight. The reaction solution was poured into ice water and crystal precipitated was filtered. The crystal was dissolved in CH$_2$Cl$_2$ and dried, then the solvent was distilled off under reduced pressure. The residue was purified by silica gel chromatography (SiO$_2$ 217 g; eluted with toluene), and then recrystallized from CH$_2$Cl$_2$/Et$_2$O/n-hexane to give 2.64 g of a colorless columnar crystal (70.2%), m.p. 128.5~130.0° C.

Elemental analysis (C$_{22}$H$_{18}$O$_3$ (MW=330.383)): Calcd. C, 79.98; H, 5.49 Found C, 79.80; H, 5.62

IR (CHCl$_3$): 1738, 1600, 1488, 1451, 1448, 1437, 1397 cm$^{-1}$

NMR (CDCl$_3$): δ 3.827 (s, 3H), 4.597 (s, 1H), 6.97~7.22 (m, 5H), 7.26~7.60 (m, 9H)

(2) Sodium 2-(4-biphenyl)-2,3-epoxy-3 phenylpropionate (I-40)

Methyl ester (I-39) (2.59 g, 7.84 mmol) was dissolved in a solution of an aqueous 1N-NaOH solution (8.2 ml, 8.23 mmol) in MeOH (37 ml)/THF (24 ml), and the mixture was stirred for 10 minutes with ice cooling, and stirred at room temperature for 3 hours. The solvent of the reaction solution was distilled off under reduced pressure. The residue was washed with Et$_2$O to give 2.66 g of a colorless crystal (quantitative).

Melting point: >300 ° C.
Elemental analysis (C$_{21}$H$_{15}$O$_3$Na0.3H$_2$O (MW=343.743)): Calcd. C, 73.38; H, 4.57; Na, 6.69 Found C, 73.23; H, 4.49; Na, 7.07

IR (nujol): 3040, 1622, 1489, 1457, 1386cm$^{-1}$

NMR (d$_6$-DMSO): δ 4.340 (s, 1H), 6.96~7.19 (m, 5H), 7.24~7.51 (m, 7H), 7.51~7.60 (m, 2H)

(3) Titled compound 0144

To a solution of a Na salt (I-40) (2.58 g, 7.62 mmol) in THF (38 ml), oxalyl chloride (13.6 ml, 152 mmol) was dropwise added with ice cooling, and the mixture was stirred at the same temperature for 30 minutes. After stirring at room temperature for additional 1.5 hours, the solvent was distilled off under reduced pressure. After the resulting residue was dissolved in THF (38 ml), Me$_3$SiN$_3$ (5.32 ml, 38.1 mmol) was added, and the mixture was heated under reflux for 4 hours. The solvent of the reaction solution was distilled off under reduced pressure and the residue was dissolved in CHCl$_3$/MeOH (9:1). After the solution was washed with water and dried, the solvent was distilled off. The resulting crystalline residue of cream color was recrystallized from THF/Et$_2$O to give 1.362 g of a colorless needless crystal.

Melting point: 201.0°~204.0° C.
Elemental analysis (C$_{21}$H$_{15}$NO$_2$ (MW=313.356)): Calcd.: C, 80.49; H, 4.83; N, 4.47 Found: C, 80.44; H, 4.99; N, 4.57

IR (CHCl$_3$): 3463, 3190, 2335, 1765 (sh), 1748, 1676, 1600, 1498, 1489, 1449 cm$^{-1}$

NMR (CDCl$_3$): δ 7.27~7.72 (m, 14H), 10.316 (brs, 1H)

EXAMPLE 119
4-(4-Biphenyl)-3-benzine-5-phenyl-oxazolin-2-one (I-43) (0145)

To a solution of oxazoline (1.02 g, 3.17 mmol) produced in Example 118 in DMF (10 ml), NaH (60%, 140 mg, 3.49 mmol) and benzyl bromide (1.13 ml, 9.51 mmol) were added, and the mixture was stirred for 2.5 hours with ice cooling. The reaction solution was poured into ice water and the solution was extracted with EtOAc. The EtOAc layer was washed with water and dried, and the solvent was distilled off under reduced pressure to give 2.17 g of a yellow oily product, which was purified by silica gel chromatography (SiO$_2$ 138 g; eluted with toluene and toluene/EtOAc (19:1)) to give 1.02 g of an oily residue of cream color (80%).

Elemental analysis (C$_{28}$N$_{21}$NO$_2$ (MW=403.481)): Calcd. C, 83.35; H, 5.25; N, 3.47 Found: C, 83.33; H, 5.13; N, 3.50

IR (CHCl$_3$): 1748, 1660, 1600, 1498, 1488, 1448, 1435, 1381 cm$^{-1}$

NMR (CDCl$_3$): δ 4.701 (s, 2H), 6.98~7.11 (m, 2H), 7.14~7.56 (m, 13H), 7.58~7.72 (m, 4H)

EXAMPLE 120
Compound 0093

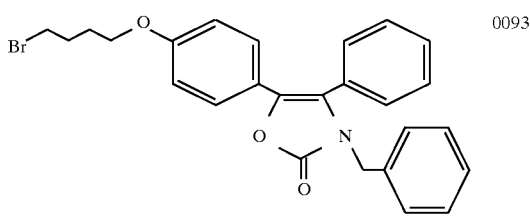

According to the method similar to that described in Example 110, an oxazoline derivative was obtained and the oxazoline derivative was benzylated according to the method similar to that described in Example 15 to give the titled compound. oily substance IR: (CHCl$_3$): 1745, 1610, 1513 cm$^{-1}$.
Mass m/z 477 (M$^+$)

EXAMPLE 121
4,5-Diphenyl-3-N-phenylethyl-3-oxazolin-2-one (0075)
This compound was a known compound.

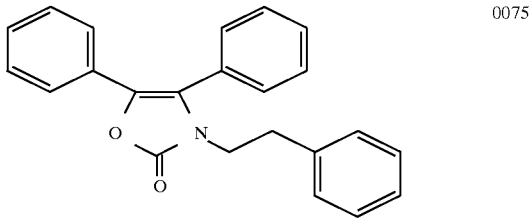

Advantages

Arachidonic acid was a precursor of prostaglandins and leukotrienes which are inflamation inducers. Production of these inducers is initiated by the action of phospholipase A$_2$ (PLA$_2$).

PLA$_2$ is a protein that hydrolyzes the 2-acyl ester bond of phospholipids. Most familiar PLA$_2$ is Ca$^{2+}$-dependent secretory PLA$_2$. However, secretory PLA$_2$ does not selectively cleave phospholipids containing arachidonic acid, and therefore, it is thought to have little significance in the initiation of prostaglandin and leukotriene biosynthesis.

Recently, a novel type of PLA$_2$ found in cytosol was discovered in various types of cells such as platelets, macrophages, interstitial cells of the renal glomeruli, monoblast and macrophage cell lines and kidney [Clark, J. D. et al., Cell 65: 1043–1051, 1991]. This cytosolic PLA$_2$ (cPLA$_2$) preferentially hydrolyzes phospholipids containing arachidonic acid esterified in the 2-position [Sharp, J. D. et al., J. Biol. Chem. 266: 14850–14853, 1991]. It is also thought that cPLA$_2$ translocates to the cell membrane in response to physiological (cytosolic) increments in Ca$^{2+}$ concentration and it is involved in the selective cleavage of arachidonic acid.

It is therefore expected that inhibition of this cytosolic PLA$_2$ activity may lead to the inhibition of arachidonic acid liberation and hence to the decreased production of prostaglandins and leukotrienes. The inhibition of cytosolic PLA$_2$ is also considered to reduce the production of platelet activating factor (PAF), one of the inflamation inducers.

Assay of cPLA₂ activity

Taking the above matter into consideration, the compounds of the present invention were evaluated for their effect on cytosolic PLA₂ activity as described in published literature [Kramer, R. M., Robers, E. F., Manetta, J. and Putanam, J. E. et al., J. Biol. Chem. 268 (8): 5268–5272, 1991]. Briefly, PLA₂ activity was assayed using sonicated liposomes containing 1-palmitoyl-2-[$^{14}$C]arachidonyl-sn-glycero-3-phosphocholine and sn-1,2-dioleoyl glycerol at a molar ratio of 2:1. The assay mixture contained 1 mM CaCl₂, 2 mM 2-mercaptoethanol, 150 mM NaCl, 50 mM Hepes, pH 7.4, and 0.1 mg/ml BSA. The substrate consisted of 2 μM radiolabeled phosphatidycholine liposomes containing 1 μM dioleoyl glycerol.

The amount of released fatty acids in the reaction as mentioned above was quantitated by a liquid scintillation counter. Separately, the same assay was performed except that the compound of the present invention was not added to serve as the enzyme control. The inhibitioory activity was expressed as a percent (%) of PLA₂ activity in the enzyme control, and thereby 50% inhibition concentration was calculated.

TABLE 11

Cytosolic PLA₂ inhibition activity

| Example No. | (compound No.) | IC₅₀ (μM) | % Inhibition at 2 μM |
|---|---|---|---|
| 1 | (0037) | 207 | None |
| 15 | (0067) | >50 | None |
| 16 | (0071) | 13 | 18% |
| 17 | (0070) | 4.3 | 46% |
| 18 | (0069) | 153 | None |
| 27 | (0095) | 35 | 26% |
| 28 | (0097) | 28 | 48% |
| 33 | (0142) | 220 | None |
| 34 | (0153) | 126 | None |
| 35 | (0155) | 57 | None |
| 36 | (0156) | 120 | None |
| 40 | (0044) | 54 | 19% |
| 41 | (0086) | 8.3 | 19% |
| 42 | (0099) | 42 | 12% |
| 43 | (0109) | 250 | None |
| 51 | (0039) | 6.2 | 24% |
| 52 | (0047) | 35 | 17% |
| 53 | (0048) | 17 | None |
| 54 | (0062) | 50 | None |
| 55 | (0090) | 65 | 14% |
| 56 | (0091) | 105 | 11% |
| 62 | (0054) | 124 | None |
| 73 | (0028) | 103 | None |
| 75 | (0073) | 50 | None |
| 77 | (0140) | 89 | None |
| 81 | (0029) | 103 | None |
| 82 | (0030) | 103 | None |
| 84 | (0079) | 218 | None |

TABLE 11-continued

Cytosolic PLA₂ inhibition activity

| Example No. | (compound No.) | IC₅₀ (μM) | % Inhibition at 2 μM |
|---|---|---|---|
| 88 | (0092) | 8.3 | 28% |
| 89 | (0108) | 59 | None |
| 92 | (0212) | 43 | 21% |
| 93 | (0168) | 66 | None |
| 94 | (0169) | 85 | None |
| 95 | (0181) | 101 | None |
| 96 | (0182) | 66 | None |
| 97 | (0199) | 32 | 32% |
| 98 | (0213) | 9.3 | 24% |
| 99 | (0246) | 50 | 20% |
| 100 | (0247) | 10 | 23% |
| 101 | (0288) | 2.0 | 50% |
| 102 | (0289) | 6.6 | 36% |
| 103 | (0296) | 11 | 21% |
| 104 | (0313) | about 50 | 13% |
| 105 | (0315) | 90 | 22% |
| 106 | (0325) | 8.7 | 32% |
| 107 | (0346) | 3.0 | 47% |
| 108 | (0347) | 7.4 | 33% |
| 109 | (0303) | 50 | 18% |
| 121 | (0075) | 14 | 21% |
|  | (0001) | 6.0 | 34% |
|  | (0002) | 68 | None |
| sample 1 | (0003) | 52 | Nones |

We claim:

1. A compound represented by the formula:

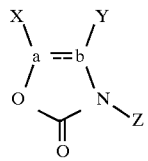

wherein a and b are each a carbon atom;

a bond:
- - - - between a and b indicates that it is a single bond or a double bond;

X and Y independently are an optionally substituted phenyl group; and Z is a C₃–C₆ alkyl group substituted by phenyl, an optionally substituted C₈–C₁₅ alkenyl group, and an optionally substituted C₂–C₇ alkynyl group.

* * * * *